United States Patent
Yoneda et al.

(10) Patent No.: US 11,912,684 B2
(45) Date of Patent: Feb. 27, 2024

(54) N-(4-PYRIDYL)NICOTINAMIDE COMPOUND OR SALT THEREOF

(71) Applicant: ISHIHARA SANGYO KAISHA, LTD., Osaka (JP)

(72) Inventors: Tetsuo Yoneda, Osaka (JP); Kotaro Yoshida, Osaka (JP); Yuta Tazawa, Osaka (JP); Tatsuya Kani, Osaka (JP); Yoko Cho, Osaka (JP); Yuto Murai, Osaka (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 460 days.

(21) Appl. No.: 16/608,593

(22) PCT Filed: Apr. 25, 2018

(86) PCT No.: PCT/JP2018/016844
§ 371 (c)(1),
(2) Date: Oct. 25, 2019

(87) PCT Pub. No.: WO2018/199175
PCT Pub. Date: Nov. 1, 2018

(65) Prior Publication Data
US 2021/0115015 A1 Apr. 22, 2021

(30) Foreign Application Priority Data
Apr. 27, 2017 (JP) ................. 2017-088847

(51) Int. Cl.
*C07D 401/12* (2006.01)
*A01N 43/40* (2006.01)
*A01P 5/00* (2006.01)

(52) U.S. Cl.
CPC .......... *C07D 401/12* (2013.01); *A01N 43/40* (2013.01); *A01P 5/00* (2021.08)

(58) Field of Classification Search
CPC .. C07D 401/12; C07D 213/82; C07D 401/14; A01N 43/40; A01N 47/12; A01N 43/56; A01P 5/00
See application file for complete search history.

(56) References Cited

U.S. PATENT DOCUMENTS

| | | |
|---|---|---|
| 5,852,042 A | 12/1998 | Jakobi et al. |
| 8,598,209 B2 | 12/2013 | Burgey et al. |
| 10,273,218 B2 | 4/2019 | Westwell et al. |
| 2004/0006047 A1 | 1/2004 | Schaper et al. |
| 2008/0021024 A1 | 1/2008 | Sucholeiki et al. |
| 2011/0206783 A1 | 8/2011 | Burgey et al. |
| 2014/0142097 A1 | 5/2014 | Hoelzemann et al. |
| 2017/0267653 A1 | 9/2017 | Westwell et al. |

FOREIGN PATENT DOCUMENTS

| | | |
|---|---|---|
| CA | 2733557 A1 | 2/2010 |
| EA | 023364 B1 | 5/2016 |
| JP | 2003-73357 A | 3/2003 |
| JP | 2004-331541 A | 11/2004 |
| JP | 2014-518884 A | 8/2014 |
| JP | 2017-8029 A | 1/2017 |
| JP | 2017-008029 A | 1/2017 |
| WO | 02/070483 A1 | 9/2002 |
| WO | 2005/115986 A1 | 12/2005 |
| WO | 2008/002671 A2 | 1/2008 |
| WO | 2010018714 A1 | 2/2010 |
| WO | 2010051188 A1 | 5/2010 |
| WO | 2010/071837 A1 | 6/2010 |
| WO | 2012034959 A2 | 3/2012 |
| WO | 2016016728 A2 | 2/2016 |
| WO | 2016/175017 A1 | 11/2016 |

OTHER PUBLICATIONS

Patani, G. A., et al. "Bioisosterism: A rational approach in Drug Design" Chem. Rev., 1996, 96(8), 3147-3176. (Year: 1996).*
A. G. Ismail et al., "The Synthesis of Pyrido [4, 3-d] pyrimidin-4(3H)-ones from 4-Aminonicotinic Acid", Journal of the Chemical Society [Section] C: Organic, Jan. 1, 1967, (24), pp. 2613-2617.
International Search Report (PCT/ISA/210) dated Jul. 31, 2018 issued by the International Searching Authority in International Application No. PCT/JP2018/016844.
Written Opinion (PCT/ISA/237) dated Jul. 31, 2018 issued by the International Searching Authority in International Application No. PCT/JP2018/016844.
Office Action dated Jan. 29, 2021 issued by the Russian Patent Office in corresponding Russian Patent Application No. 2019137957. Found in STN: RN 1990713-66-0, date of entry Nov. 9, 2016, RN 1986316-28-2, date of entry Apr. 9, 2016, RN 1962976-43-7, date of entry Jul. 29, 2016, RN 1462356-74-6, date of entry Oct. 22, 2013.

(Continued)

*Primary Examiner* — Erin E Hirt
(74) *Attorney, Agent, or Firm* — Sughrue Mion, PLLC

(57) ABSTRACT

Although a variety of pest control agents have been used for many years, many of these pest control agents have various problems, such as insufficient effectiveness, and restriction on use thereof due to resistance acquired by pests, and the like. Therefore, it is desired to develop a novel pest control agent that is less likely to have such drawbacks. One of objects of the present invention is to provide a highly active compound or a salt thereof against a pest. The present invention relates to an N-(4-pyridyl)nicotinamide compound represented by the following formula (I) (in the formula (I), for each substituent, see Description) or a salt thereof.

(I)

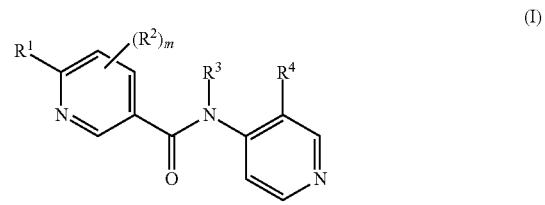

4 Claims, No Drawings

(56) References Cited

OTHER PUBLICATIONS

Found in PubChem: PubChem CID: 55233130, date of entry Jan. 24, 2012, PubChem CID: 63670021, date of entry Oct. 22, 2012, PubChem CID: 63980531, date of entry Oct. 23, 2012, PubChem CID: 81227309, date of entry Oct. 20, 2014, PubChem CID: 81241211, date of entry Oct. 20, 2014, PubChem CID: 81757645, date of entry Oct. 20, 2014, PubChem CID: 81757566, date of entry Oct. 20, 2014, PubChem CID: 99834194, date of entry Dec. 11, 2015.
English abstract of JP 2003-073357 A, published Mar. 12, 2003.
English abstract of JP 2004-331541 A, published Nov. 11, 2004.
English abstract of JP 2017-008029 A, published Jan. 12, 2017.
Office Action dated Apr. 13, 2021, issued by African Regional Intellectual Property Organization (ARIPO) in corresponding ARIPO Patent Application No. AP/P/2019/011978.
Office Action dated Mar. 17, 2021, issued by the India Intellectual Property Office in Indian Patent Application No. 201947047478.
Theodoridis, G., "Chapter 4 Fluorine-Containing Agrochemicals: An Overview of Recent Developments", 2006, Fluorine and the Environment, vol. 2, pp. 121-175, 55 pages total.
Communication dated Nov. 30, 2021 by the Colombian Patent Office in Colombian Patent Application No. NC2019/0011969.
Communication dated May 25, 2022 issued by the Russian Intellectual Property Office in corresponding Russian Application No. 2019137957.
V.G. Belikov, Pharmaceutical Chemistry, Training manual, Fourth revised edition, MEDpress-inform, 2007, pp. 27-29, 11 pages total.
G.V. Komarova, "Crop Pest Control", Allotment, AST Stalker, 2005, pp. 3-5, 10 pages total.
G. S. Gruzdev, "Chemical Protection of Plants", Third Revised Edition, Moscow Agropromizdat, 1987, chapter 1, pp. 9-11.chapter 2, p. 119 (paragraphs 1 and 3), 415 p., 14 pages total.
A. M. Prokhorov et al., "The Great Soviet Encyclopedia", Third Edition, Moscow, "Sovetskaya Entsiklopediya" Publishing House, 1971, 3rd edition, p. 426 (col. 1266)—p. 429 (col. 1275), 10 pages total.

\* cited by examiner

N-(4-PYRIDYL)NICOTINAMIDE COMPOUND OR SALT THEREOF

TECHNICAL FIELD

The present invention relates to a novel N-(4-pyridyl)nicotinamide compound or a salt thereof. In addition, the present invention relates to a pest control agent, an agricultural and horticultural insecticide, a miticide, a nematicide, or a soil pesticide comprising the compound or a salt thereof as an active ingredient. Further, the present invention relates to a method for controlling a pest by applying an effective amount of the compound or a salt thereof.

BACKGROUND ART

Patent Document 1 describes a wide range of heteroarylamide compounds for insecticide uses and Patent Document 2 describes a wide range of compounds having a pyridine skeleton for medicament uses. Also, Patent Document 3 describes a wide range of heteroarylamide compounds for medicament uses.

CITED REFERENCES

Patent Documents

Patent Document 1: WO2002/070483
Patent Document 2: WO2005/115986
Patent Document 3: JP-A-2003-73357

DISCLOSURE OF THE INVENTION

Problems to be Solved by the Invention

Although a large number of pest control agents have been used for many years, many of these pest control agents have various problems such as insufficient effectiveness and restriction on use thereof due to resistance acquired by pests, and the like. Therefore, it is desired to develop a novel pest control agent that is less likely to have such drawbacks.

Objects of the present invention are to provide a highly active compound or a salt thereof against a pest, to provide a pest control agent, an agricultural and horticultural insecticide, a miticide, a nematicide, or a soil pesticide using the compound or a salt thereof, and to provide a method for controlling a pest by applying the compound or a salt thereof.

Incidentally, the compounds described in Patent Document 1 and the compounds described in Patent Document 2 are distinguished from the compounds of the present invention. In addition, in Patent Document 3, there is only a specific description of a compound where $R^4$ is a hydrogen atom in the formula (I) to be mentioned below.

Means for Solving the Problems

In order to find a more excellent pest control agent, the present inventors have extensively studied pyridine compounds. As a result, they have found that a novel N-(4-pyridyl)nicotinamide compound or a salt thereof has an extremely high control effect against pests at low dose.

That is, the present invention relates to the followings.
[1] An N-(4-pyridyl)nicotinamide compound represented by formula (I):

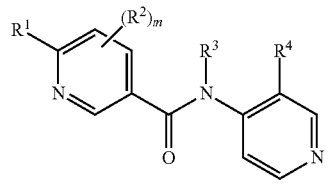

wherein $R^1$ is a hydrogen atom, a halogen atom, an alkyl, a haloalkyl, an alkoxy, a haloalkoxy, an aryloxy, or a haloalkylaryl;
$R^2$ is a halogen atom, an alkyl, a haloalkyl, an alkoxy, a haloalkoxy, an amino, a monoalkylamino, a dialkylamino, an aryloxy, a cyano, an alkylthio, an alkylsulfinyl, or an alkylsulfonyl;
$R^3$ is a hydrogen atom, an alkyl, a cycloalkyl, a haloalkyl, an alkoxy, an alkoxyalkyl, an alkylcarbonyl, or an alkoxycarbonyl;
$R^4$ is a halogen atom, a nitro, an alkyl, an alkenyl, an alkynyl, a haloalkyl, an alkoxy, an alkylthio, an alkylcarbonyl, a haloalkylcarbonyl, a cycloalkylcarbonyl, an alkoxycarbonyl, an (alkylthio)carbonyl, or a pyrazolyl;
m is an integer of 0 to 3; and
the $R^2$s may be the same as or different from each other when multiple $R^2$s exist,
or a salt thereof.
[2] The compound or a salt thereof as described in the above [1], wherein, in the formula (I),
$R^1$ is a hydrogen atom, a halogen atom, an alkyl, a haloalkyl, an alkoxy, a haloalkoxy, an aryloxy, or a haloalkylaryl;
$R^2$ is a halogen atom, an alkyl, a haloalkyl, an alkoxy, an amino, a monoalkylamino, a dialkylamino, a cyano, an alkylthio, an alkylsulfinyl, or an alkylsulfonyl;
$R^3$ is a hydrogen atom, an alkyl, a cycloalkyl, an alkoxy, an alkoxyalkyl, an alkylcarbonyl, or an alkoxycarbonyl;
$R^4$ is a halogen atom, a nitro, an alkyl, an alkenyl, a haloalkyl, an alkoxy, an alkylthio, an alkylcarbonyl, a haloalkylcarbonyl, an alkoxycarbonyl, an (alkylthio)carbonyl, or a pyrazolyl; and
m is 0 or 1.
[3] The compound or a salt thereof as described in the above [1], wherein, in the formula (I),
$R^1$ is a hydrogen atom, a halogen atom, an alkyl, a haloalkyl, an alkoxy, a haloalkoxy, an aryloxy, or a haloalkylaryl;
$R^2$ is a halogen atom, an alkyl, a haloalkyl, an alkoxy, an amino, a cyano, an alkylthio, an alkylsulfinyl, or an alkylsulfonyl;
$R^3$ is a hydrogen atom, an alkyl, a cycloalkyl, an alkoxy, or an alkoxycarbonyl;
$R^4$ is a halogen atom, a nitro, an alkyl, an alkenyl, a haloalkyl, an alkoxy, an alkylthio, an alkylcarbonyl, an alkoxycarbonyl, an (alkylthio)carbonyl, or a pyrazolyl; and
m is 0 or 1.
[4] The compound or a salt thereof as described in the above [1], wherein, in the formula (I),
$R^1$ is a halogen atom, an alkyl, a haloalkyl, an alkoxy, a haloalkoxy, an aryloxy, or a haloalkylaryl;
$R^2$ is a halogen atom, an alkyl, a haloalkyl, an alkoxy, an amino, a monoalkylamino, a dialkylamino, a cyano, an alkylthio, an alkylsulfinyl, or an alkylsulfonyl;

$R^3$ is a hydrogen atom, an alkyl, a cycloalkyl, an alkoxy, an alkoxyalkyl, an alkylcarbonyl, or an alkoxycarbonyl;

$R^4$ is a nitro, an alkyl, an alkenyl, a haloalkyl, an alkoxy, an alkylthio, an alkylcarbonyl, a haloalkylcarbonyl, an alkoxycarbonyl, an (alkylthio)carbonyl, or a pyrazolyl; and m is 0 or 1.

[5] The compound or a salt thereof as described in the above [1], wherein, in the formula (I), $R^1$ is a halogen atom, an alkyl, a haloalkyl, an alkoxy, a haloalkoxy, an aryloxy, or a haloalkylaryl;

$R^2$ is a halogen atom, an alkyl, a haloalkyl, an alkoxy, an amino, a cyano, an alkylthio, an alkylsulfinyl, or an alkylsulfonyl;

$R^3$ is a hydrogen atom, an alkyl, a cycloalkyl, an alkoxy, or an alkoxycarbonyl;

$R^4$ is a nitro, an alkyl, an alkenyl, a haloalkyl, an alkoxy, an alkylthio, an alkylcarbonyl, an alkoxycarbonyl, an (alkylthio)carbonyl, or a pyrazolyl; and m is 0 or 1.

[6] The compound or a salt thereof as described in the above [1], wherein, in the formula (I), $R^1$ is a halogen atom, an alkyl, a haloalkyl, an alkoxy, or a haloalkoxy;

$R^2$ is a halogen atom, an alkyl, a haloalkyl, an alkoxy, a haloalkoxy, an amino, a monoalkylamino, or a dialkylamino;

$R^3$ is a hydrogen atom, an alkyl, an alkoxyalkyl, an alkylcarbonyl, or an alkoxycarbonyl;

$R^4$ is a halogen atom, a nitro, an alkyl, an alkenyl, an alkynyl, a haloalkyl, an alkoxy, an alkylthio, an alkylcarbonyl, a haloalkylcarbonyl, a cycloalkylcarbonyl, an alkoxycarbonyl, an (alkylthio)carbonyl, or a pyrazolyl;

m is an integer of 0 to 3; and the $R^2$s may be the same as or different from each other when multiple $R^2$s exist.

[7] The compound or a salt thereof as described in the above [1], wherein, in the formula (I), $R^1$ is a halogen atom, an alkyl, a haloalkyl, an alkoxy, or a haloalkoxy;

$R^2$ is an alkyl, a haloalkyl, an alkoxy, an amino, a monoalkylamino, or a dialkylamino;

$R^3$ is a hydrogen atom, an alkyl, an alkoxyalkyl, an alkylcarbonyl, or an alkoxycarbonyl;

$R^4$ is a halogen atom, a nitro, an alkyl, a haloalkyl, an alkoxy, an alkylthio, an alkoxycarbonyl, an (alkylthio)carbonyl, or a pyrazolyl; and m is 0 or 1.

[8] The compound or a salt thereof as described in the above [1], wherein, in the formula (I), $R^1$ is an alkyl, a haloalkyl, or a haloalkoxy;

$R^2$ is an alkyl, a haloalkyl, or an amino;

$R^3$ is a hydrogen atom or an alkyl;

$R^4$ is a halogen atom, a nitro, an alkyl, an alkoxy, an alkoxycarbonyl, or a pyrazolyl; and m is 0 or 1.

[9] The compound or a salt thereof as described in any one of the above [1] to [8], wherein, in the formula (I), $R^1$ is a haloalkyl; $R^3$ is a hydrogen atom, an alkyl, a cycloalkyl, or an alkoxy; $R^4$ is an alkyl, an alkoxy, an alkylcarbonyl, or an alkoxycarbonyl; and m is 0.

[10] The compound or a salt thereof as described in the above [1], wherein, in the formula (I), $R^1$ is a hydrogen atom, a halogen atom, an alkyl, a haloalkyl, a haloalkoxy, an aryloxy, or a haloalkylaryl.

[11] The compound or a salt thereof as described in the above [1], wherein, in the formula (I), $R^1$ is an alkyl, a haloalkyl, or a haloalkoxy.

[12] The compound or a salt thereof as described in any one of the above [1], [10], or [11], wherein, in the formula (I), $R^2$ is a halogen atom, an alkyl, a haloalkyl, an alkoxy, an amino, a cyano, an alkylthio, an alkylsulfinyl, or an alkylsulfonyl.

[13] The compound or a salt thereof as described in any one of the above [1] and [10] to [12], wherein, in the formula (I), $R^2$ is an alkyl, a haloalkyl, or an amino.

[14] The compound or a salt thereof as described in any one of the above [1], [10] to [13], wherein, in the formula (I), $R^3$ is a hydrogen atom, an alkyl, a cycloalkyl, an alkoxy, or an alkoxycarbonyl.

[15] The compound or a salt thereof as described in any one of the above [1], [10] to [14], wherein, in the formula (I), $R^3$ is a hydrogen atom or an alkyl.

[16] The compound or a salt thereof as described in any one of the above [1], [10] to [15], wherein, in the formula (I), $R^4$ is a halogen atom, a nitro, an alkyl, an alkenyl, a haloalkyl, an alkoxy, an alkylthio, an alkylcarbonyl, an alkoxycarbonyl, an (alkylthio)carbonyl, or a pyrazolyl.

[17] The compound or a salt thereof as described in any one of the above [1], [10] to [16], wherein, in the formula (I), $R^4$ is a halogen atom, a nitro, an alkyl, an alkoxy, an alkoxycarbonyl, an (alkylthio)carbonyl, or a pyrazolyl.

[18] The compound or a salt thereof as described in any one of the above [1], [10] to [17], wherein, in the formula (I), m is 0 or 1.

[19] The compound or a salt thereof as described in the above [6], wherein, in the formula (I), $R^1$ is a halogen atom, an alkyl, a haloalkyl, an alkoxy, or a haloalkoxy; $R^2$ is an alkyl, a haloalkyl, an alkoxy, an amino, a monoalkylamino, or a dialkylamino; $R^3$ is a hydrogen atom, an alkyl, an alkoxyalkyl, an alkylcarbonyl, or an alkoxycarbonyl; $R^4$ is a halogen atom, a nitro, an alkyl, a haloalkyl, an alkoxy, an alkylthio, an alkoxycarbonyl, an (alkylthio)carbonyl, or a pyrazolyl; and m is 0 or 1.

[20] The compound or a salt thereof as described in the above [6], wherein, in the formula (I), $R^1$ is an alkyl, a haloalkyl, or a haloalkoxy; $R^2$ is an alkyl, a haloalkyl, or an amino; $R^3$ is a hydrogen atom or an alkyl; $R^4$ is a halogen atom, a nitro, an alkyl, an alkoxy, an alkoxycarbonyl, or a pyrazolyl; and m is 0 or 1.

[21] A pest control agent comprising the compound or a salt thereof as described in any one of the above [1] to [20] as an active ingredient.

[22] An agricultural and horticultural insecticide, miticide, nematicide, or soil pesticide comprising the compound or a salt thereof as described in any one of the above [1] to [20] as an active ingredient.

[23] An agricultural insecticide comprising the compound or a salt thereof as described in any one of the above [1] to [20] as an active ingredient.

[24] A method for controlling a pest by applying an effective amount of the compound or a salt thereof as described in any one of the above [1] to [20].

Effect of the Invention

The pest control agent comprising the compound represented by the above formula (I) or a salt thereof has an extremely high control effect against pests at low dose.

EMBODIMENTS FOR CARRYING OUT THE INVENTION

Hereinafter, the present invention is described in detail, but they merely show preferable examples and the present invention should not be construed as being limited thereto.

Incidentally, in the Description of the present application, "Cn" (n is natural number) has the same meaning as that of "carbon number n" (n is natural number). When "ppm" is described for the concentration, it means "ppm by weight".

The present invention relates to an N-(4-pyridyl)nicotinamide compound represented by the following formula (I):

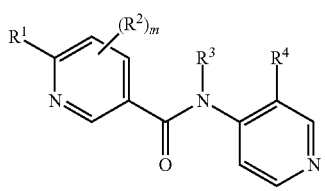

wherein $R^1$ is a hydrogen atom, a halogen atom, an alkyl, a haloalkyl, an alkoxy, a haloalkoxy, an aryloxy, or a haloalkylaryl;

$R^2$ is a halogen atom, an alkyl, a haloalkyl, an alkoxy, a haloalkoxy, an amino, a monoalkylamino, a dialkylamino, an aryloxy, a cyano, an alkylthio, an alkylsulfinyl, or an alkylsulfonyl;

$R^3$ is a hydrogen atom, an alkyl, a cycloalkyl, a haloalkyl, an alkoxy, an alkoxyalkyl, an alkylcarbonyl, or an alkoxycarbonyl;

$R^4$ is a halogen atom, a nitro, an alkyl, an alkenyl, an alkynyl, a haloalkyl, an alkoxy, an alkylthio, an alkylcarbonyl, a haloalkylcarbonyl, a cycloalkylcarbonyl, an alkoxycarbonyl, an (alkylthio)carbonyl, or a pyrazolyl;

m is an integer of 0 to 3; and the $R^2$s may be the same as or different from each other when multiple $R^2$s exist, or a salt thereof (hereinafter, in some cases, all of them are also referred to as "the compound of the present invention").

As the halogen atom or the halogen as a substituent in the above formula (I), each atom of fluorine, chlorine, bromine, or iodine may be mentioned. The number of the halogen atom as the substituent may be 1 or 2 or more. In the case of 2 or more, individual halogen atoms may be the same or different from each other. Further, the substitution position of the halogen atom may be any position.

Incidentally, "haloalkyl" used in the Description of the present application means an alkyl at least one hydrogen atom of which is substituted with the halogen atom(s). Similarly, "haloalkoxy", "haloalkylaryl" and "haloalkylcarbonyl" mean an alkoxy, an alkylaryl and an alkylcarbonyl at least one hydrogen atom of each group is substituted with the halogen atom(s), respectively. The halogen atom substituted from the hydrogen atom in these haloalkyl, haloalkoxy, haloalkylaryl or haloalkylcarbonyl is referred to as "the halogen as a substituent".

Examples of the alkyl or alkyl portion in the above formula (I) include linear or branched $C_1$-$C_6$ groups such as methyl, ethyl, normal propyl, isopropyl, normal butyl, isobutyl, secondary butyl, tertiary butyl, normal pentyl, isopentyl, neopentyl, normal hexyl, or neohexyl.

Examples of the alkenyl or alkenyl portion in the above formula (I) include linear or branched $C_2$-$C_6$ groups such as vinyl, 1-propenyl, 2-propenyl, isopropenyl, 2-methyl-1-propenyl, 1-methyl-1-propenyl, 2-methyl-2-propenyl, 1-methyl-2-propenyl, 1-butenyl, 2-butenyl, 3-butenyl, 1-pentenyl, 2-pentenyl, 2-methyl-2-butenyl, 1-hexenyl, or 2,3-dimethyl-2-butenyl.

Examples of the alkynyl or alkynyl portion in the above formula (I) include linear or branched $C_2$-$C_6$ groups such as ethynyl, 1-propynyl, 2-propynyl, 1-butynyl, 2-butynyl, 3-butynyl, 1-methyl-2-propynyl, 2-methyl-3-butynyl, 3,3-dimethyl-1-butynyl, 1-hexynyl, 2-hexynyl, 3-hexynyl, 4-hexynyl, or 5-hexynyl.

Examples of the cycloalkyl or cycloalkyl portion in the above formula (I) include $C_3$-$C_6$ groups such as cyclopropyl, cyclobutyl, cyclopentyl, or cyclohexyl.

Examples of the aryl or aryl portion in the above formula (I) include $C_6$-$C_{10}$ groups such as phenyl and naphthyl.

As the salt of the compound represented by the above formula (I), any salts may be included as far as they are acceptable in the technical field. Examples thereof include ammonium salts such as dimethylammonium and triethylammonium; inorganic salts such as hydrochlorides, perchlorates, sulfates, and nitrates; organic salts such as acetates, trifluoroacetates, oxalates, p-toluenesulfonates, and methanesulfonates; and the like.

There is a case where isomers such as optical isomers may be present as the compound of the present invention, and both of individual isomers and an isomer mixture are included in the compound of the present invention. In the Description of the present application, the isomers are described as a mixture unless specifically stated. Incidentally, within the range of common technical knowledge in the technical field, various isomers other than the above ones are also included in the compound of the present invention. Further, depending on the kind of the isomers, there is a case where they have a chemical structure different from that of the compound of the present invention but, since one ordinary in the art can sufficiently recognize that they are in an isomeric relationship, it is obvious that they fall within the present invention.

The compound of the present invention can be produced according to the following production methods and usual production methods of salts, but methods are not limited to these methods.

Production Method [1]

The compound represented by the above formula (I) can be produced by reacting a compound represented by the following formula (II) with a compound represented by the following formula (III) in the presence of a dehydration condensation agent or a base. Incidentally, commercially available products can be used as the compound represented by the following formula (II) and the compound represented by the following formula (III), and also the compounds can be produced by known methods.

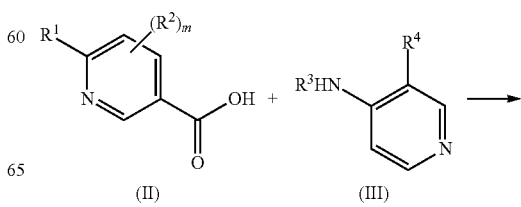

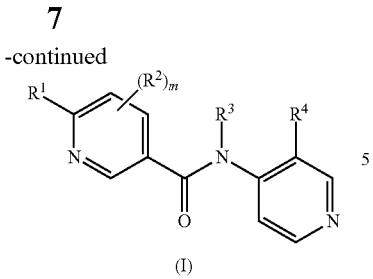

(I)

In the formula of the production method [1], $R^1$, $R^2$, $R^3$, $R^4$, and m are as mentioned above.

The dehydration condensation agent is not particularly limited but examples thereof include 1-ethyl-3-(3-dimethylaminopropyl)carbodiimide hydrochloride, 1,3-dicyclohexylcarbodiimide, 0-(7-azabenzotriazol-1-yl)-N,N,N',N'-tetramethyluronium hexafluorophosphate, and the like.

The reaction can be carried out with adding an additive, as required. Examples of the additive include 1-hydroxybenzotriazole, N-hydroxysuccinimide, N,N-dimethyl-4-aminopyridine, and the like.

The base is not particularly limited but examples thereof include tertiary amines such as triethylamine, 4-methylmorpholine, and diisopropylethylamine, 1,8-diazabicyclo[5.4.0]-7-undecene, pyridine, 4-(dimethylamino)pyridine, 2,6-lutidine, and the like.

The reaction can be carried out in the presence of a solvent, as required. The solvent is not particularly limited but, for example, there may be used one or two or more appropriately selected from ethers such as diethyl ether, butyl methyl ether, tetrahydrofuran, ethylene glycol dimethyl ether, 1,4-dioxane, and dimethoxyethane; aliphatic halogenated hydrocarbons such as methylene chloride, dichloroethane, and chloroform; aromatic hydrocarbons such as benzene, toluene, xylene, and chlorobenzene; aprotic polar solvents such as N,N-dimethylformamide, N,N-dimethylacetamide, N-methyl-2-pyrrolidone, dimethyl sulfoxide, and sulfolane; nitriles such as acetonitrile and propionitrile; esters such as ethyl acetate and ethyl propionate; aliphatic hydrocarbons such as pentane, hexane, heptane, octane, and cyclohexane; ketones such as acetone and ethyl methyl ketone; water; and the like or a mixture thereof may be used.

As for the reaction temperature, the reaction can be usually carried out in a range of 0° C. to a temperature at which the reaction system is refluxed under heating. As for the reaction time, the reaction can be usually carried out for several minutes to 24 hours.

Production Method [2]

The compound represented by the above formula (I) can be produced by reacting a compound represented by the following formula (II-a) with a compound represented by the following formula (III) in the presence of a base.

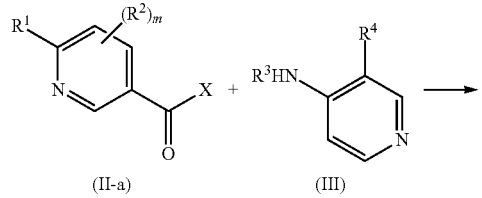

(II-a)  (III)

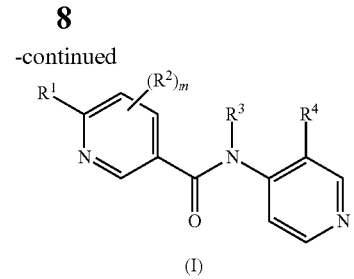

(I)

In the formula of the production method [2], $R^1$, $R^2$, $R^3$, $R^4$, and m are as mentioned above; X is a halogen atom.

The base may be an organic base or an inorganic base. The organic base is not particularly limited but example thereof include amine bases such as triethylamine and diisopropylethylamine. The inorganic base is not particularly limited but examples thereof include alkali metal carbonates such as sodium carbonate, potassium carbonate, and cesium carbonate.

The reaction can be carried out in the presence of a solvent, as required. The solvent is not particularly limited but, for example, there may be used one or two or more appropriately selected from ethers such as diethyl ether, butyl methyl ether, tetrahydrofuran, ethylene glycol dimethyl ether, 1,4-dioxane, and dimethoxyethane; aliphatic halogenated hydrocarbons such as methylene chloride, dichloroethane, and chloroform; aromatic hydrocarbons such as benzene, toluene, xylene, and chlorobenzene; aprotic polar solvents such as N,N-dimethylformamide, N,N-dimethylacetamide, N-methyl-2-pyrrolidone, dimethyl sulfoxide, and sulfolane; nitriles such as acetonitrile and propionitrile; esters such as ethyl acetate and ethyl propionate; aliphatic hydrocarbons such as pentane, hexane, heptane, octane, and cyclohexane; ketones such as acetone and ethyl methyl ketone; water; and the like, or a mixture thereof may be used.

As for the reaction temperature, the reaction can be usually carried out in a range of 0° C. to a temperature at which the reaction system is refluxed under heating. As for the reaction time, the reaction can be usually carried out for several minutes to 24 hours.

A commercially available product can be used as the compound represented by the above formula (II-a), and also the compound can be produced by reacting a compound represented by the above formula (II) with a halogenating agent as shown in the following scheme.

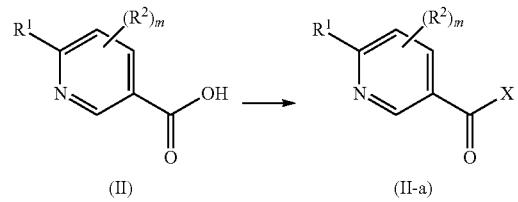

(II)  (II-a)

In the formula of the production method of the compound represented by the above formula (II-a), $R^1$, $R^2$, X, and m are as mentioned above.

The halogenating agent is not particularly limited but examples thereof include thionyl chloride, oxalyl chloride, phosphoryl chloride, sulfuryl chloride, phosphorus trichloride, phosphorus pentachloride, and the like.

The reaction can be carried out in the presence of a solvent, as required. The solvent is not particularly limited but, for example, there may be used one or two or more appropriately selected from ethers such as diethyl ether, butyl methyl ether, tetrahydrofuran, ethylene glycol dimethyl ether, 1,4-dioxane, and dimethoxyethane; aliphatic halogenated hydrocarbons such as methylene chloride, dichloroethane, and chloroform; aromatic hydrocarbons such as benzene, toluene, xylene, and chlorobenzene; aprotic polar solvents such as N,N-dimethylformamide, N,N-dimethylacetamide, N-methyl-2-pyrrolidone, dimethyl sulfoxide, and sulfolane; nitriles such as acetonitrile and propionitrile; esters such as ethyl acetate and ethyl propionate; aliphatic hydrocarbons such as pentane, hexane, heptane, octane, and cyclohexane; ketones such as acetone and ethyl methyl ketone; and the like, or a mixture thereof may be used.

As for the reaction temperature, the reaction can be usually carried out in a range of 0° C. to a temperature at which the reaction system is refluxed under heating. As for the reaction time, the reaction can be usually carried out for several minutes to 24 hours.

The compound represented by the above formula (III) can be produced by reacting a compound represented by the following formula (III-a) with a compound represented by the following formula (IV). Commercially available products can be used as the compound represented by the following formula (III-a) and the compound represented by the following formula (IV), and also the compounds can be produced by known methods.

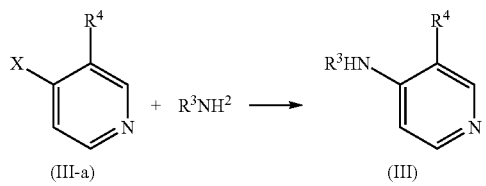

In the formula of the production method of the compound represented by the above formula (III), $R^3$, $R^4$, and X are as mentioned above.

The reaction can be carried out in the presence of a base, as required. Examples of the base include alkali metal hydrides such as sodium hydride; alkali metal carbonates such as sodium carbonate, potassium carbonate, and cesium carbonate; alkali metal hydroxides such as lithium hydroxide, sodium hydroxide, and potassium hydroxide; tertiary amines such as triethylamine, 4-methylmorpholine, and diisopropylethylamine; 1,8-diazabicyclo[5.4.0]-7-undecene, pyridine, 4-(dimethylamino)pyridine, 2,6-lutidine, and the like.

The reaction can be carried out in the presence of a solvent, as required. The solvent is not particularly limited but, for example, there may be used one or two or more appropriately selected from ethers such as diethyl ether, butyl methyl ether, tetrahydrofuran, ethylene glycol dimethyl ether, 1,4-dioxane, and dimethoxyethane; aliphatic halogenated hydrocarbons such as methylene chloride, dichloroethane, and chloroform; aromatic hydrocarbons such as benzene, toluene, xylene, and chlorobenzene; aprotic polar solvents such as N,N-dimethylformamide, N,N-dimethylacetamide, N-methyl-2-pyrrolidone, dimethyl sulfoxide, and sulfolane; nitriles such as acetonitrile and propionitrile; esters such as ethyl acetate and ethyl propionate; aliphatic hydrocarbons such as pentane, hexane, heptane, octane, and cyclohexane; ketones such as acetone and ethyl methyl ketone; water; and the like, or a mixture thereof may be used.

As for the reaction temperature, the reaction can be usually carried out in a range of 0° C. to a temperature at which the reaction system is refluxed under heating. As for the reaction time, the reaction can be usually carried out for several minutes to 24 hours.

Preferred embodiments of pest control agents comprising the compounds of the present invention as an active ingredient will be described below.

The pest control agents comprising the compounds of the present invention as an active ingredient are useful, for example, as agents for controlling pests, mites, nematodes, or soil pests which are problematic in agricultural and horticultural fields, that is, agricultural and horticultural insecticides, miticides, nematicides, or soil pesticides and so on. Further, the agents are useful as control agents for animal parasitic organisms, that is, animal parasitic organism-killing agents.

The compounds of the present invention are useful for controlling pests, e.g., aphids such as green peach aphid (*Myzus persicae*) and cotton aphid (*Aphis gossypii*); agricultural pests such as diamondback moth (*Plutella xylostella*), cabbage armyworm (*Mamestra brassicae*), common cutworm (*Spodoptera litura*), codling moth (*Laspeyresia pomonella*), corn earworm moth (*Heliothis zea*), tobacco budworm (*Heliothis virescens*), gypsy moth (*Lymantria dispar*), rice leafroller (Cnaphalocrocis *medinalis*), smaller tea tortrix (*Adoxophyes honmai*), colorado potato beetle (*Leptinotarsa decemlineata*), cucurbit leaf beetle (*Aulacophora femoralis*), boll weevil (*Anthonomus grandis*), planthoppers such as brown planthopper (*Nilaparvata lugens*), leafhoppers, scales, stinkbugs, whiteflies such as sweetpotato whitefly (*Bemisia tabaci*), drips, grasshoppers, anthomyiid flies, scarabaeidae scarabs, black cutworm (*Agrotis ipsilon*), turnip moth cutworm (*Agrotis segetum*), and ants; gastropods such as slugs and snails; sanitary hygienic pests such as tropical rat mite (*Ornithonyssus bacoti*), cockroaches, housefly (*Musca domestica*), and common house mosquito (*Culex pipiens*); stored grain pests such as angoumois grain moth (*Sitotroga cerealella*), adzuki bean weevil (*Callosobruchus chinensis*), red flour beetle (*Tribolium castaneum*), and mealworms; household pests such as casemaking clothes moth (*Tinea translucens*), black carpet beetle (*Attagenus unicolor*), and termites; and the like, mites, e.g., plant parasitic mites such as two-spotted spider mite (*Tetranychus urticae*), carmine spider mite (*Tetranychus cinnabarinus*), kanzawa spider mite (*Tetranychus kanzawai*), citrus red mite (*Panonychus citri*), European red mite (*Panonychus ulmi*), broad mite (*Polyphagotarsonemus latus*), pink citrus rust mite (*Aculops pelekassi*), and bulb mite (*Rhizoglyphus echinopus*); house dust mites such as mold mite (*Tyrophagus putrescentiae*), *Dermatophagoides farinae*, and *Chelacaropsis moorei*; and the like, nematodes, e.g., plant parasitic nematodes such as root-knot nematodes, cyst nematodes, root-lesion nematodes, white-tip nematode (*Aphelenchoides besseyi*), strawberry bud nematode (*Nothotylenchus acris*), and pine wood nematode (*Bursaphelenchus lignicolus*); and the like, soil pests, e.g., isopods such as wood lice (*Armadillidium vulgare*) and sowbugs (*Porcellio scaber*); and the like.

The pest control agents comprising the compounds of the present invention as an active ingredient are particularly effective for controlling plant parasitic mites, agricultural pests, plant parasitic nematodes, and the like. Among them, the compounds exhibits further excellent effect on control of plant parasitic mites and agricultural pests, so that the compounds are very useful as insecticides and miticides.

Moreover, the agricultural and horticultural insecticides, miticides, nematicides, and soil pesticides comprising the compounds of the present invention as an active ingredient are also effective for controlling various pests having acquired resistance to chemical agents such as organophosphorus agents, carbamate agents, synthetic pyrethroid agents, neonicotinoid agents and so on.

Furthermore, the compounds of the present invention have excellent systemic properties, and therefore, by the application of the agricultural and horticultural insecticides, miticides, nematicides, or soil pesticides comprising the compounds of the present invention as an active ingredient to a soil treatment, soil pests, mites, nematodes, gastropods, and isopods and, at the same time, foliage pests can be controlled.

As other preferred embodiments of pest control agents comprising the compounds of the present invention as an active ingredient, there may be mentioned agricultural and horticultural insecticides, miticides, nematicides, and soil pesticides which collectively control the above-described plant parasitic mites, agricultural pests, plant parasitic nematodes, gastropods, soil pests, and the like.

The pest control agent comprising the compound of the present invention as an active ingredient is usually formulated by mixing the compound with various additives and used in the form of formulation such as dusts, granules, water dispersible granules, wettable powders, water-based suspension concentrates, oil-based suspension concentrates, water soluble granules, water soluble powders, emulsifiable concentrates, soluble concentrates, pastes, aerosols, or ultra low volume formulations. However, so long as it is suitable for the purpose of the present invention, it may be formulated into any type of formulation which is commonly used in this field.

The additives to be used for the formulation include solid carriers such as diatomaceous earth, slaked lime, calcium carbonate, talc, white carbon, kaolin, bentonite, kaolinite, sericite, clay, sodium carbonate, sodium bicarbonate, mirabilite, zeolite, and starch; solvents such as water, toluene, xylene, solvent naphtha, dioxane, acetone, isophorone, methyl isobutyl ketone, chlorobenzene, cyclohexane, dimethyl sulfoxide, N,N-dimethylformamide, N,N-dimethylacetamide, N-methyl-2-pyrrolidone, and alcohol; anionic surfactants such as salts of fatty acid, benzoate, alkylsulfosuccinate, dialkylsulfosuccinate, polycarboxylate, salts of alkylsulfuric acid ester, alkyl sulfate, alkylaryl sulfate, alkyl diglycol ether sulfate, salts of alcohol sulfuric acid ester, alkylsulfonate, alkylarylsulfonate, arylsulfonate, lignin sulfonate, alkyldiphenyl ether disulfonate, polystyrene sulfonate, salts of alkylphosphoric acid ester, alkylaryl phosphate, styrylaryl phosphate, salts of polyoxyethylene alkyl ether sulfuric acid ester, polyoxyethylene alkylaryl ether sulfate, salts of polyoxyethylene alkylaryl ether sulfuric acid ester, polyoxyethylene alkyl ether phosphate, salts of polyoxyethylene alkylaryl phosphoric acid ester, and salts of condensate of naphthalene sulfonate with formaldehyde; nonionic surfactants such as sorbitan fatty acid ester, glycerin fatty acid ester, fatty acid polyglyceride, fatty acid alcohol polyglycol ether, acetylene glycol, acetylene alcohol, oxyalkylene block polymer, polyoxyethylene alkyl ether, polyoxyethylene alkylaryl ether, polyoxyethylene styrylaryl ether, polyoxyethylene glycol alkyl ether, polyethylene glycol, polyoxyethylene fatty acid ester, polyoxyethylene sorbitan fatty acid ester, polyoxyethylene glycerin fatty acid ester, polyoxyethylene hydrogenated castor oil, and polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffin; and the like.

As for the ingredients of such additives, one or two or more may be appropriately selected for use, so long as the purpose of the present invention can thereby be accomplished. Further, in addition to the above-described additives, some one can be appropriately selected from ones which are known in this field, and used. For example, various additives which are commonly used, such as a filler, a thickener, an anti-settling agent, an antifreezing agent, a dispersion stabilizer, a phytotoxicity reducing agent, and an anti-mold agent may also be employed.

The mixing ratio (weight ratio) of the compound of the present invention to the various additives is from 0.001:99.999 to 95:5, preferably from 0.005:99.995 to 90:10. In the actual application of such a formulation, it may be used as it is, or may be diluted to a predetermined concentration with a diluent such as water, as required, added with various spreaders (surfactants, plant oils, mineral oils, etc.), and then used.

The application of the agricultural and horticultural insecticides, miticides, nematicides, and soil pesticides comprising the compounds of the present invention as an active ingredient cannot generally be defined, as it varies depending upon the weather conditions, the type of the formulation, the time for application, the application site, the types or degree of outbreak of diseases and pests. However, it is usually applied in a concentration of the active ingredient being from 0.05 to 800,000 ppm, preferably from 0.5 to 500,000 ppm, and the dose thereof per unit area is such that the compound of the present invention is from 0.05 to 50,000 g, preferably from 1 to 30,000 g, per hectare.

Further, the present invention also includes a method for controlling pests by such application methods, especially, a method for controlling pests, mites, nematodes or soil pests which are problematic in agricultural and horticultural fields, particularly, a method for controlling plant parasitic mites, agricultural pests, or plant parasitic nematodes.

The various formulations of the pest control agents comprising the compounds of the present invention as an active ingredient or their diluted compositions may be applied by application methods which are commonly employed, such as spreading (such as spraying, misting, atomizing, granule scattering, or application on water surface), soil application (such as mixing or irrigation), surface application (such as coating, dust coating, or covering), or use of an impregnated toxic bait. Further, it is possible to feed domestic animals with a food into which the above active ingredient is mixed to thereby control the outbreak or growth of noxious pests, particularly noxious insects, with excrements of the animals. Furthermore, the agent may also be applied by a so-called ultra low volume application method. In this method, the agent may be composed of 100% of the active ingredient.

Further, the agricultural and horticultural insecticides, miticides, nematicides, and soil pesticides comprising the compounds of the present invention as an active ingredient may be mixed with or may be used in combination with other agricultural chemicals, fertilizers, or phytotoxicity-reducing agents, and the like, and in this case, more excellent effects or activities may sometimes be obtained. Such other agricultural chemicals include a herbicide, an insecticide, a miticide, a nematicide, a soil pesticide, a fungicide, an antivirus agent, an attractant, an antibiotic, a plant hormone, a plant growth regulator, and the like. Especially, an insecticide composition, miticide composition, nematicide composition, or soil pesticide composition having a compound of the present invention mixed with or used in combination with one or two or more active ingredient compounds of other agricultural chemicals can improve the application range, the timing for application of the agent, the controlling activities, and the like to preferred directions. The compound of the present invention and the active compounds of other agricultural chemicals may separately be formulated and they may be mixed for use at the time of application, or the both may be formulated together for use. The present invention also includes such an insecticide composition, miticide composition, nematicide composition, or soil pesticide composition.

Examples of the active ingredient compounds (common names, some of them are still in an application stage, or test codes of the Japan Plant Protection Association) of the insecticides, miticides, nematicides, or soil pesticides in above-described other agricultural chemicals include:

organic phosphate ester-based compounds such as profenofos, dichlorvos, fenamiphos, fenitrothion, EPN (O-ethyl O-4-nitrophenyl phenylphosphonothioate), diazinon, chlorpyrifos, chlorpyrifos-methyl, acephate, prothiofos, fosthiazate, cadusafos, dislufoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, ESP (oxydeprofos), azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet, phorate, phoxim, and triazophos;

carbamate-based compounds such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC (3,5-xylyl methylcarbamate), and fenothiocarb;

nereistoxin derivatives such as cartap, thiocyclam, bensultap, thiosultap-sodium, thiosultap-disodium, monosultap, bisultap, and thiocyclam hydrogen oxalate;

organochlorine-based compounds such as dicofol, tetradifon, endosulfan, dienochlor, and dieldrin;

organometallic compounds such as fenbutatin oxide and cyhexatin;

pyrethroid-based compounds such as fenvalerate, permethrin, cypermethrin, deltamethrin, cyhalothrin, tefluthrin, ethofenprox, flufenprox, cyfluthrin, fenpropathrin, flucythrinate, fluvalinate, cyclopothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin, flumethrin, and decamethrin;

benzoylurea-based compounds such as diflubenzuron, chlorfluazuron, teflubenzuron, flufenoxuron, triflumuron, hexaflumuron, lufenuron, novaluron, noviflumuron, bistrifluron, and fluazuron;

juvenile hormone-like compounds such as methoprene, pyriproxyfen, fenoxycarb, and diofenolan;

pyridazinone-based compounds such as pyridaben;

pyrazole-based compounds such as fenpyroximate, fipronil, tebufenpyrad, ethiprole, tolfenpyrad, acetoprole, pyrafluprole, and pyriprole;

neonicotinoid-based compounds such as imidacloprid, nitenpyram, acetamiprid, thiacloprid, thiamethoxam, clothianidin, nidinotefuran, dinotefuran, and nithiazine;

hydrazine-based compounds such as tebufenozide, methoxyfenozide, chromafenozide, and halofenozide;

pyridine-based compounds such as pyridalyl and flonicamid;

cyclic keto enol-based compounds such as spirodiclofen, spiromesifen, spirotetramat, and spiropidion;

strobilurin-based compounds such as fluacrypyrim;

pyridinamine-based compounds such as flufenerim;

dinitro-based compounds, organosulfur compounds, urea-based compounds, triazine-based compounds, hydrazone-based compounds, and, as other compounds, there may be mentioned compounds such as flometoquin, buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, propargite, clofentezine, metaflumizone, flubendiamide, cyflumetofen, chlorantraniliprole, cyantraniliprole, cyclaniliprole, cyenopyrafen, pyrifluquinazon, fenazaquin, amidoflumet, sulfluramid, hydramethylnon, metaldehyde, ryanodine, verbutin, chlorobenzoate, thiazolylcinnanonitrile, sulfoxaflor, fluensulfone, triflumezopyrim, afidopyropen, flupyradifuron, fluxametamide, tetraniliprole, fluralaner, broflanilide, pyflubumide, dicloromezotiaz, fluhexafon, tioxazafen, fluazaindolizine, acynonapyr, benzpyrimoxan, oxazosulfyl, flupyrimin, and tyclopyrazoflor.

Furthermore, the compounds of the present invention may be mixed with or used in combination with microorganism agricultural chemicals such as crystal protein toxins produced by *Bacillus thuringiensis* such as *Bacillus thuringiensis aizawai, Bacillus thuringiensis* kurstaki, *Bacillus thuringiensis israelensis, Bacillus thuringiensis* japonensis, or *Bacillus thuringiensis* tenebrionis, insect pathogenic virus agents, insect pathogenic filamentous fungus agents, and nematode pathogenic filamentous fungus agents; antibiotics and semi-synthetic antibiotics such as avermectin, emamectin benzoate, milbemectin, milbemycin, spinosad, ivermectin, lepimectin, DE-175, abamectin, emamectin, and spinetoram; natural products such as azadirachtin and rotenone; repellents such as deet; and the like.

Examples of the active ingredient compounds (common names, some of them are still in an application stage, or test codes of the Japan Plant Protection Association) of the fungicides in the above-described other agricultural chemicals include:

anilinopyrimidine-based compounds such as mepanipyrim, pyrimethanil, cyprodinil, and ferimzone;

triazolopyrimidine-based compounds such as 5-chloro-7-(4-methylpiperidin-1-yl)-6-(2,4,6-trifluorophenyl)[1,2,4]triazolo[1,5-a]pyrimidine;

pyridinamine-based compounds such as fluazinam;

azole-based compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, triclazole, probenazole, simeconazole, pefurazoate, ipconazole, and imibenconazole;

quinoxaline-based compounds such as quinomethionate;

dithiocarbamate-based compounds such as maneb, zineb, mancozeb, polycarbamate, metiram, propineb, and thiram;

organochlorine-based compounds such as fthalide, chlorothalonil, and quintozene;

imidazole-based compounds such as benomyl, cyazofamid, thiophanate-methyl, carbendazim, thiabendazole, and fuberiazole;

cyanoacetamide-based compounds such as cymoxanil;

anilide-based compounds such as metalaxyl, metalaxyl-M, mefenoxam, oxadixyl, ofurace, benalaxyl, benalaxyl-M (another name: kiralaxyl or chiralaxyl), furalaxyl, cyprofuram, carboxin, oxycarboxin, thifluzamide, boscalid, bixafen, isothianil, tiadinil, and sedaxane;

sulfamide-based compounds such as dichlofluanid;

copper-based compounds such as cupric hydroxide and oxine copper;

isoxazole-based compounds such as hymexazol;

organophosphorus-based compounds such as fosetyl-Al, tolclofos-methyl, S-benzyl O, O-diisopropyl phosphorothioate, O-ethyl S, S-diphenyl phosphorodithioate, aluminum ethyl hydrogen phosphonate, edifenphos, and iprobenfos;

phthalimide-based compounds such as captan, captafol, and folpet;

dicarboxyimide-based compounds such as procymidone, iprodione, and vinclozolin;

benzanilide-based compounds such as flutolanil and mepronil;

amide-based compounds such as penthiopyrad, a mixture of 3-(difluoromethyl)-1-methyl-N-[(1RS,4SR,9RS)-1,2,3,4-tetrahydro-9-isopropyl-1,4-methanonaphthalen-5-yl]pyrazol-4-carboxamide and 3-(difluoromethyl)-1-methyl-N-[(1RS,4SR,9SR)-1,2,3,4-tetrahydro-9-isopropyl-1,4-methanonaphthalen-5-yl]pyrazol-4-carboxamide (isopyrazam), silthiopham, fenoxanil, and furametpyr;

benzamide-based compounds such as fluopyram and zoxamide;

piperadine-based compounds such as triforine;

pyridine-based compounds such as pyrifenox;

carbinol-based compounds such as fenarimol;

piperidine-based compounds such as fenpropidin;

morpholine-based compounds such as fenpropimorph and tridemorph;

organotin-based compounds such as fentin hydroxide and fentin acetate;

urea-based compounds such as pencycuron;

cinnamic acid-based compounds such as dimethomorph and flumorph;

phenylcarbamate-based compounds such as diethofencarb;

cyanopyrrole-based compounds such as fludioxonil and fenpiclonil;

strobilurin-based compounds such as azoxystrobin, kresoxim-methyl, metominostrobin, trifloxystrobin, picoxystrobin, oryzastrobin, dimoxystrobin, pyraclostrobin, and fluoxastrobin;

oxazolidinone-based compounds such as famoxadone;

thiazolecarboxamide-based compounds such as ethaboxam;

valine amide-based compounds such as iprovalicarb and benthiavalicarb-isopropyl;

acylamino acid-based compounds such as methyl N-(isopropoxycarbonyl)-L-valyl-(3RS)-3-(4-chlorophenyl)-O-alaninate (valiphenalate);

imidazolinone-based compounds such as fenamidone;

hydroxyanilide-based compounds such as fenhexamid;

benzenesulfonamide-based compounds such as flusulfamide;

oxime ether-based compounds such as cyflufenamid;

anthraquinone-based compounds;

crotonic acid-based compounds;

antibiotics such as validamycin, kasugamycin, and polyoxins;

guanidine-based compounds such as iminoctadine and dodine;

quinoline-based compounds such as 6-tertiary butyl-8-fluoro-2,3-dimethylquinolin-4-yl acetate (tebufloquin);

thiazolidine-based compounds such as (Z)-2-(2-fluoro-5-(trifluoromethyl)phenylthio)-2-(3-(2-methoxyphenyl)thiazolidin-2-ylidene)acetonitrile (flutianil); and as other compounds, there may be mentioned pyribencarb, isoprothiolane, pyroquilon, diclomezine, quinoxyfen, propamocarb hydrochloride, chloropicrin, dazomet, metam-sodium, nicobifen, metrafenone, UBF-307, diclocymet, proquinazid, amisulbrom (another name: amibromdole), 3-(2,3,4-trimethoxy-6-methylbenzoyl)-5-chloro-2-methoxy-4-methylpyridine, 4-(2,3,4-trimethoxy-6-methylbenzoyl)-2,5-dichloro-3-trifluoromethylpyridine, pyriofenone, isofetamid, mandipropamid, fluopicolide, carpropamid, meptyldinocap, spiroxamine, fenpyrazamine, mandestrobin, ZF-9646, BCF-051, BCM-061, BCM-062, and the like.

Besides, as agricultural chemicals capable of being mixed with or being used in combination with the compounds of the present invention, for example, there are active ingredient compounds of herbicides described in The Pesticide Manual (15th edition), particularly soil-treating type ones, and the like.

EXAMPLES

Examples of the present invention will be described in the following but the present invention should not be construed as being limited thereto. First, Synthetic Examples of the compounds of the present invention will be described.

Synthetic Example 1

Synthesis of Methyl 4-(6-(trifluoromethyl)nicotinamide)nicotinate (Compound No. I-9)

Methyl 4-aminonicotinate (366 mg, 2.4 mmol), 0-(7-azabenzotriazol-1-yl)-N,N,N,N-tetramethyluronium hexafluorophosphate (997 mg, 2.6 mmol), and triethylamine (1.22 mL, 8.7 mmol) were added to a solution of 6-(trifluoromethyl)nicotinic acid (418 mg, 2.2 mmol) in N,N-dimethylformamide (15 mL), followed by stirring at room temperature for 24 hours. The reaction mixture was poured into water (50 mL) and the resulting solid was filtrated to afford the desired product (426 mg, yield: 60%).

Synthetic Example 2

Synthesis of Methyl 4-(N-ethyl-6-(trifluoromethyl)nicotinamide)nicotinate (Compound No. I-11)

(1) An aqueous 70% ethylamine solution (9.9 g, 153.9 mmol) was added to a solution of methyl 4-chloronicotinate (3.3 g, 19.2 mmol) in N,N-dimethylformamide (40 mL), followed by stirring at 70° C. for 2 hours. The reaction mixture was poured into water (200 mL), followed by extraction with ethyl acetate. The organic layer was washed with saturated saline, dried over anhydrous sodium sulfate, and filtered. The solvent was removed under reduced pressure to afford methyl 4-(ethylamino)nicotinate (3.0 g, Yield: 87%).

(2) To a mixture of methyl 4-(ethylamino)nicotinate (300 mg, 1.7 mmol) and diisopropylethylamine (0.85 mL, 5.0 mmol) in tetrahydrofuran (6 mL) was added 6-(trifluoromethyl)nicotinic acid chloride (350 mg, 1.7 mmol), followed by stirring at 65° C. for 5 hours. The reaction mixture was poured into water (20 mL), followed by extraction with ethyl acetate. The organic layer was washed with saturated saline, dried over anhydrous sodium sulfate, and filtered. After the solvent was removed under reduced pressure, the residue was purified by flash chromatography (eluent: n-heptane/ethyl acetate) to afford the desired product (437 mg, Yield: 74%).

Synthetic Example 3

Synthesis of Methyl 4-(N-methoxy-6-(trifluoromethyl)-nicotinamide)nicotinate (Compound No. I-131)

(1) Water (13 mL), sodium hydroxide (2.7 g, 67.0 mmol), and triethylamine (4.7 mL, 33.5 mmol) were sequentially added to a solution of O-methylhydroxylamine hydrochloride (8.4 g, 100.5 mmol) in N-methyl-2-pyrrolidone (67 mL), followed by stirring at room temperature for 15 minutes. Methyl 4-chloronicotinate (5.75 g, 33.5 mmol) was added to the reaction mixture, followed by stirring at 75° C. for 15 hours. The reaction mixture was poured into water (300 mL), followed by extraction with ethyl acetate. The organic layer was washed with saturated saline, dried over anhydrous sodium sulfate, and filtered. After the solvent was removed under reduced pressure, the residue was purified by flash chromatography (eluent: n-heptane/ethyl acetate) to afford methyl 4-(methoxyamino)nicotinate (1.7 g, Yield: 28%).

(2) To a mixture of methyl 4-(methoxyamino)nicotinate (500 mg, 2.7 mmol) and diisopropylethylamine (1.44 mL, 8.2 mmol) in tetrahydrofuran (9 mL) was added 6-(trifluoromethyl)nicotinic acid chloride (863 mg, 4.1 mmol), followed by stirring at 65° C. for 16 hours. The reaction mixture was poured into water (45 mL), followed by extraction with ethyl acetate. The organic layer was washed with saturated saline, dried over anhydrous sodium sulfate, and filtered. After the solvent was removed under reduced pressure, the residue was purified by flash chromatography (eluent: n-heptane/ethyl acetate) to afford the desired product (330 mg, Yield: 34%).

Now, typical examples of the compounds represented by the formula (I) according to the present invention will be shown in Table 1. These compounds can be synthesized in accordance with the above-described Synthetic Examples or the above-described various production methods. In Table 1, numerical values described in the column of physical properties indicate melting points (° C.) and, for the compounds with description of "NMR", $^1$H-NMR spectral data thereof are shown in Table 2.

Incidentally, "No." in Table 1 indicates compound number. Further, in the table, Me represents a methyl group, Et represents an ethyl group, Pr represents a propyl group, Bu represents a butyl group, "cyc-" represents "cyclo", "i-" represents "iso", "t-" represents "tertiary", and "n-" represents "normal", respectively.

Moreover, in the column of $(R^2)_m$, for example, the compound described as "6-$NH_2$" represents that it is substituted with $R^2$ only at the substitution position attached to the chemical structural formula in the table, that is, it is a compound of "m=1" where it is substituted with amino only at 6-position. On the other hand, the compound described as "m=0" represents a compound which is not substituted with $R^2$. The other similar descriptions follow this.

In the $^1$H-NMR spectrum of Compound No. I-54, respective peaks were measured as a mixture of optical isomers.

TABLE 1 (I)

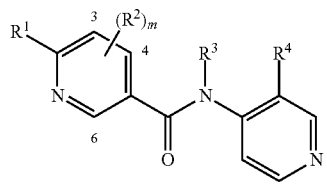

| No. | $R^1$ | $(R^2)m$ | $R^3$ | $R^4$ | Physical properties |
|---|---|---|---|---|---|
| I-1 | $CF_3$ | m = 0 | H | Me | 129.2 |
| I-2 | $CF_3$ | m = 0 | H | F | 157.1 |
| I-3 | $CF_3$ | m = 0 | H | Cl | NMR |
| I-4 | $CF_3$ | m = 0 | H | Br | NMR |
| I-5 | $CF_3$ | m = 0 | H | I | 170.7 |
| I-6 | $CF_3$ | m = 0 | H | $NO_2$ | 110.2 |
| I-7 | $CF_3$ | m = 0 | H | OEt | 165.4 |
| I-8 | $CF_3$ | 6-$NH_2$ | H | OEt | NMR |
| I-9 | $CF_3$ | m = 0 | H | $CO_2Me$ | 120.9 |
| I-10 | $CF_3$ | m = 0 | Me | $CO_2Me$ | 105-106 |
| I-11 | $CF_3$ | m = 0 | Et | $CO_2Me$ | 98-99 |
| I-12 | $CF_3$ | 6-Me | H | $CO_2Me$ | 171.9 |
| I-13 | $CF_3$ | 6-Et | H | $CO_2Me$ | 135.9 |
| I-14 | $CF_3$ | 6-i-Pr | H | $CO_2Me$ | 138.6 |
| I-15 | $CF_3$ | 6-$CF_3$ | H | $CO_2Me$ | 140-153.5 |
| I-16 | $CF_3$ | m = 0 | H | COSMe | 134.0 |
| I-17 | Cl | m = 0 | H | $CO_2Me$ | NMR |
| I-18 | Cl | m = 0 | H | OEt | |
| I-19 | Me | m = 0 | H | $CO_2Me$ | NMR |
| I-20 | Me | m = 0 | H | OEt | |
| I-21 | OMe | m = 0 | H | $CO_2Me$ | 121.8 |
| I-22 | OMe | m = 0 | H | OEt | |
| I-23 | $CF_3$ | 6-OMe | H | $CO_2Me$ | NMR |
| I-24 | $CF_3$ | 6-OMe | H | OEt | |
| I-25 | $CF_3$ | m = 0 | H | (pyrazolyl) | 286.5 |
| I-26 | $OCH_2CF_3$ | m = 0 | H | Br | NMR |
| I-27 | $OCH_2CF_3$ | m = 0 | H | $CO_2Me$ | NMR |
| I-28 | $OCH_2CF_3$ | m = 0 | H | OEt | |
| I-29 | t-Bu | m = 0 | H | I | NMR |
| I-30 | t-Bu | m = 0 | H | $CO_2Me$ | 239.5 |
| I-31 | t-Bu | m = 0 | H | OEt | |
| I-32 | $CF_3$ | 6-NHMe | H | $CO_2Me$ | |
| I-33 | $CF_3$ | 6-$NMe_2$ | H | $CO_2Me$ | |
| I-34 | $CF_3$ | m = 0 | $CH_2OMe$ | $CO_2Me$ | |
| I-35 | $CF_3$ | m = 0 | COMe | $CO_2Me$ | |
| I-36 | $CF_3$ | m = 0 | $CO_2Me$ | $CO_2Me$ | NMR |
| I-37 | $CF_3$ | m = 0 | H | $CF_3$ | 77.6 |
| I-38 | $CF_3$ | m = 0 | H | SEt | 128.2 |
| I-39 | H | 3-$CF_3$ | H | $CO_2Me$ | 127.4 |
| I-40 | $CF_3$ | m = 0 | H | $CO_2$-i-Pr | 122 |
| I-41 | i-$C_3F_7$ | m = 0 | H | $CO_2Me$ | 118.4 |
| I-42 | i-$C_3F_7$ | m = 0 | Me | $CO_2Me$ | |
| I-43 | i-$C_3F_7$ | m = 0 | Et | $CO_2Me$ | 90.5 |
| I-44 | H | 3-$CF_3$ | Et | $CO_2Me$ | 71.7 |

TABLE 1 (I)-continued

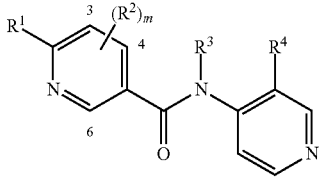

| No. | R¹ | (R²)m | R³ | R⁴ | Physical properties |
|---|---|---|---|---|---|
| I-45 | Me | m = 0 | Et | $CO_2Me$ | 93.7 |
| I-46 | (4-$CF_3$)Ph | m = 0 | H | $CO_2Me$ | 274 |
| I-47 | $CF_3$ | 6-Cl | H | $CO_2Me$ | 138.7 |
| I-48 | n-$C_3F_7$ | m = 0 | H | $CO_2Me$ | 106.4 |
| I-49 | n-$C_3F_7$ | m = 0 | Me | $CO_2Me$ | |
| I-50 | n-$C_3F_7$ | m = 0 | Et | $CO_2Me$ | NMR |
| I-51 | OPh | m = 0 | Et | $CO_2Me$ | NMR |
| I-52 | $CF_3$ | 6-Me | Et | $CO_2Me$ | 104.3 |
| I-53 | H | 4-$CF_3$ | H | $CO_2Me$ | |
| I-54 | H | 4-$CF_3$ | Et | $CO_2Me$ | NMR |
| I-55 | $CF_3$ | 3-Br | H | $CO_2Me$ | 173.4 |
| I-56 | $CF_3$ | 3-F | H | $CO_2Me$ | NMR |
| I-57 | $CF_3$ | 6-SEt | H | $CO_2Me$ | 130 |
| I-58 | n-$C_3F_7$ | m = 0 | H | OEt | 108.7 |
| I-59 | n-$C_3F_7$ | m = 0 | Me | OEt | |
| I-60 | n-$C_3F_7$ | m = 0 | Et | OEt | |
| I-61 | $C_2F_5$ | m = 0 | H | OEt | 140.6 |
| I-62 | $C_2F_5$ | m = 0 | Me | OEt | |
| I-63 | $C_2F_5$ | m = 0 | Et | OEt | |
| I-64 | $C_2F_5$ | m = 0 | H | $CO_2Me$ | 113 |
| I-65 | $C_2F_5$ | m = 0 | Me | $CO_2Me$ | |
| I-66 | $C_2F_5$ | m = 0 | Et | $CO_2Me$ | 92.8 |
| I-67 | $CF_3$ | 4-SEt | H | $CO_2Me$ | 177.8 |
| I-68 | $CF_3$ | 4-SOEt | H | $CO_2Me$ | 155.7 |
| I-69 | $CF_3$ | 4-$SO_2Et$ | H | $CO_2Me$ | 182.7 |
| I-70 | $CF_3$ | m = 0 | Me | OEt | 128.2 |
| I-71 | $CF_3$ | m = 0 | Et | OEt | NMR |
| I-72 | $CF_3$ | m = 0 | Me | SEt | 92.5 |
| I-73 | $CF_3$ | m = 0 | Et | SEt | 68.8 |
| I-74 | $CF_3$ | m = 0 | H | OMe | 138.6 |
| I-75 | $CF_3$ | m = 0 | Me | OMe | 85.5 |
| I-76 | $CF_3$ | m = 0 | Et | OMe | NMR |
| I-77 | $CF_3$ | m = 0 | H | O-n-Pr | 137.7 |
| I-78 | $CF_3$ | m = 0 | Me | O-n-Pr | |
| I-79 | $CF_3$ | m = 0 | Et | O-n-Pr | |
| I-80 | $C_2F_5$ | m = 0 | H | SEt | |
| I-81 | $C_2F_5$ | m = 0 | Me | SEt | |
| I-82 | $C_2F_5$ | m = 0 | Et | SEt | |
| I-83 | $CF_3$ | m = 0 | H | COMe | 235.5 |
| I-84 | $CF_3$ | m = 0 | H | COEt | 169.7 |
| I-85 | $CF_3$ | m = 0 | H | $COCF_3$ | |
| I-86 | $CF_3$ | m = 0 | H | $COC_2F_5$ | |
| I-87 | $CF_3$ | 3-Me | H | $CO_2Me$ | 119.2 |
| I-88 | $CF_3$ | 3-CN | H | $CO_2Me$ | NMR |
| I-89 | $CF_3$ | 4-Me | H | $CO_2Me$ | 133.9 |
| I-90 | $CF_3$ | 4-CN | H | $CO_2Me$ | |
| I-91 | $CF_3$ | m = 0 | H | $CO_2Et$ | 123.1 |
| I-92 | $CF_3$ | m = 0 | H | $CO_2$n-Pr | 101.9 |
| I-93 | $CF_3$ | m = 0 | H | Et | |
| I-94 | $CF_3$ | m = 0 | H | n-Pr | 128.1 |
| I-95 | $CF_3$ | m = 0 | H | i-Bu | |
| I-96 | $CF_3$ | m = 0 | H | $CH_3$-C($CH_3$)=CH- | 197.3 |
| I-97 | $CF_3$ | m = 0 | Me | $CO_2Et$ | 86.6 |
| I-98 | $CF_3$ | m = 0 | Me | $CO_2$n-Pr | |
| I-99 | $CF_3$ | m = 0 | Me | $CO_2$i-Pr | |
| I-100 | $CF_3$ | m = 0 | Me | COMe | |
| I-101 | $CF_3$ | m = 0 | Me | COEt | |
| I-102 | $CF_3$ | m = 0 | Me | COn-Pr | |
| I-103 | $CF_3$ | m = 0 | Me | COi-Pr | |
| I-104 | $CF_3$ | m = 0 | Me | Et | |
| I-105 | $CF_3$ | m = 0 | Me | n-Pr | |
| I-106 | $CF_3$ | m = 0 | Me | i-Bu | |
| I-107 | $CF_3$ | m = 0 | Me | $CH_2$=CH-$CH_2$- | |
| I-108 | $CF_3$ | m = 0 | Et | $CO_2Et$ | NMR |
| I-109 | $CF_3$ | m = 0 | Et | $CO_2$n-Pr | |
| I-110 | $CF_3$ | m = 0 | Et | $CO_2$i-Pr | |

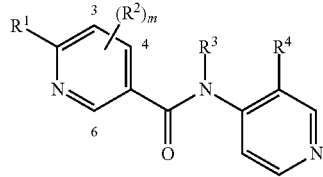

| No. | R¹ | (R²)m | R³ | R⁴ | Physical properties |
|---|---|---|---|---|---|
| I-111 | $CF_3$ | m = 0 | Et | COMe | |
| I-112 | $CF_3$ | m = 0 | Et | COEt | |
| I-113 | $CF_3$ | m = 0 | Et | COn-Pr | |
| I-114 | $CF_3$ | m = 0 | Et | COi-Pr | |
| I-115 | $CF_3$ | m = 0 | Et | Et | |
| I-116 | $CF_3$ | m = 0 | Et | n-Pr | |
| I-117 | $CF_3$ | m = 0 | Et | i-Bu | |
| I-118 | $CF_3$ | m = 0 | Et | $CH_2$=CH-$CH_2$- | |
| I-119 | $CF_3$ | m = 0 | n-Pr | $CO_2Me$ | 98.2 |
| I-120 | $CF_3$ | m = 0 | n-Pr | $CO_2Et$ | |
| I-121 | $CF_3$ | m = 0 | n-Pr | $CO_2$n-Pr | |
| I-122 | $CF_3$ | m = 0 | n-Pr | $CO_2$i-Pr | |
| I-123 | $CF_3$ | m = 0 | n-Pr | COMe | |
| I-124 | $CF_3$ | m = 0 | n-Pr | COEt | |
| I-125 | $CF_3$ | m = 0 | n-Pr | OMe | |
| I-126 | $CF_3$ | m = 0 | n-Pr | OEt | |
| I-127 | $CF_3$ | m = 0 | n-Pr | O-n-Pr | |
| I-128 | $CF_3$ | m = 0 | n-Pr | Et | |
| I-129 | $CF_3$ | m = 0 | n-Pr | n-Pr | |
| I-130 | $CF_3$ | m = 0 | n-Pr | i-Bu | |
| I-131 | $CF_3$ | m = 0 | OMe | $CO_2Me$ | 150.9 |
| I-132 | $CF_3$ | m = 0 | OMe | $CO_2Et$ | |
| I-133 | $CF_3$ | m = 0 | OMe | $CO_2$n-Pr | |
| I-134 | $CF_3$ | m = 0 | OMe | $CO_2$i-Pr | |
| I-135 | $CF_3$ | m = 0 | OMe | COMe | |
| I-136 | $CF_3$ | m = 0 | OMe | COEt | |
| I-137 | $CF_3$ | m = 0 | OMe | OMe | |
| I-138 | $CF_3$ | m = 0 | OMe | OEt | |
| I-139 | $CF_3$ | m = 0 | OMe | O-n-Pr | |
| I-140 | $CF_3$ | m = 0 | OMe | Et | |
| I-141 | $CF_3$ | m = 0 | OMe | n-Pr | |
| I-142 | $CF_3$ | m = 0 | OMe | i-Bu | |
| I-143 | $CF_3$ | m = 0 | COMe | $CO_2Et$ | |
| I-144 | $CF_3$ | m = 0 | COMe | $CO_2$n-Pr | |
| I-145 | $CF_3$ | m = 0 | COMe | $CO_2$i-Pr | |
| I-146 | $CF_3$ | m = 0 | COMe | COMe | |
| I-147 | $CF_3$ | m = 0 | COMe | COEt | |
| I-148 | $CF_3$ | m = 0 | COMe | OMe | |
| I-149 | $CF_3$ | m = 0 | COMe | OEt | |
| I-150 | $CF_3$ | m = 0 | COMe | O-n-Pr | |
| I-151 | $CF_3$ | m = 0 | COMe | Et | |
| I-152 | $CF_3$ | m = 0 | COMe | n-Pr | |
| I-153 | $CF_3$ | m = 0 | COMe | i-Bu | |
| I-154 | $CF_3$ | m = 0 | $CO_2Me$ | $CO_2Et$ | |
| I-155 | $CF_3$ | m = 0 | $CO_2Me$ | $CO_2$n-Pr | |
| I-156 | $CF_3$ | m = 0 | $CO_2Me$ | $CO_2$i-Pr | |
| I-157 | $CF_3$ | m = 0 | $CO_2Me$ | COMe | |
| I-158 | $CF_3$ | m = 0 | $CO_2Me$ | COEt | |
| I-159 | $CF_3$ | m = 0 | $CO_2Me$ | OMe | |
| I-160 | $CF_3$ | m = 0 | $CO_2Me$ | OEt | |
| I-161 | $CF_3$ | m = 0 | $CO_2Me$ | O-n-Pr | |
| I-162 | $CF_3$ | m = 0 | $CO_2Me$ | Et | |
| I-163 | $CF_3$ | m = 0 | $CO_2Me$ | n-Pr | |
| I-164 | $CF_3$ | m = 0 | $CO_2Me$ | i-Bu | |
| I-165 | $CF_3$ | m = 0 | COi-Pr | $CO_2Me$ | |
| I-166 | $CF_3$ | m = 0 | COi-Pr | $CO_2Et$ | |
| I-167 | $CF_3$ | m = 0 | COi-Pr | $CO_2$n-Pr | |
| I-168 | $CF_3$ | m = 0 | COi-Pr | $CO_2$i-Pr | |
| I-169 | $CF_3$ | m = 0 | COi-Pr | COMe | |
| I-170 | $CF_3$ | m = 0 | COi-Pr | COEt | |
| I-171 | $CF_3$ | m = 0 | COi-Pr | OMe | |
| I-172 | $CF_3$ | m = 0 | COi-Pr | OEt | |
| I-173 | $CF_3$ | m = 0 | COi-Pr | O-n-Pr | |
| I-174 | $CF_3$ | m = 0 | COi-Pr | Et | |
| I-175 | $CF_3$ | m = 0 | COi-Pr | n-Pr | |
| I-176 | $CF_3$ | m = 0 | COi-Pr | i-Bu | |

TABLE 1 (I)-continued

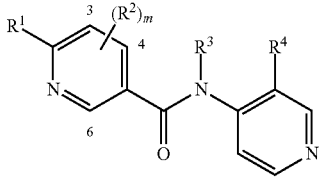

| No. | R¹ | (R²)m | R³ | R⁴ | Physical properties |
|---|---|---|---|---|---|
| I-177 | $C_2F_5$ | m = 0 | H | $CO_2Et$ | |
| I-178 | $C_2F_5$ | m = 0 | H | $CO_2$n-Pr | |
| I-179 | $C_2F_5$ | m = 0 | H | $CO_2$i-Pr | |
| I-180 | $C_2F_5$ | m = 0 | H | COMe | |
| I-181 | $C_2F_5$ | m = 0 | H | COEt | |
| I-182 | $C_2F_5$ | m = 0 | H | OMe | |
| I-183 | $C_2F_5$ | m = 0 | H | O-n-Pr | |
| I-184 | $C_2F_5$ | m = 0 | H | Et | |
| I-185 | $C_2F_5$ | m = 0 | H | n-Pr | |
| I-186 | $C_2F_5$ | m = 0 | H | i-Bu | |
| I-187 | $C_2F_5$ | m = 0 | Me | $CO_2Et$ | |
| I-188 | $C_2F_5$ | m = 0 | Me | $CO_2$n-Pr | |
| I-189 | $C_2F_5$ | m = 0 | Me | $CO_2$i-Pr | |
| I-190 | $C_2F_5$ | m = 0 | Me | COMe | |
| I-191 | $C_2F_5$ | m = 0 | Me | COEt | |
| I-192 | $C_2F_5$ | m = 0 | Me | OMe | |
| I-193 | $C_2F_5$ | m = 0 | Me | O-n-Pr | |
| I-194 | $C_2F_5$ | m = 0 | Me | Et | |
| I-195 | $C_2F_5$ | m = 0 | Me | n-Pr | |
| I-196 | $C_2F_5$ | m = 0 | Me | i-Bu | |
| I-197 | $C_2F_5$ | m = 0 | Et | $CO_2Et$ | |
| I-198 | $C_2F_5$ | m = 0 | Et | $CO_2$n-Pr | |
| I-199 | $C_2F_5$ | m = 0 | Et | $CO_2$i-Pr | |
| I-200 | $C_2F_5$ | m = 0 | Et | COMe | |
| I-201 | $C_2F_5$ | m = 0 | Et | COEt | |
| I-202 | $C_2F_5$ | m = 0 | Et | OMe | |
| I-203 | $C_2F_5$ | m = 0 | Et | O-n-Pr | |
| I-204 | $C_2F_5$ | m = 0 | Et | Et | |
| I-205 | $C_2F_5$ | m = 0 | Et | n-Pr | |
| I-206 | $C_2F_5$ | m = 0 | Et | i-Bu | |
| I-207 | $C_2F_5$ | m = 0 | n-Pr | $CO_2Me$ | |
| I-208 | $C_2F_5$ | m = 0 | n-Pr | $CO_2Et$ | |
| I-209 | $C_2F_5$ | m = 0 | n-Pr | $CO_2$n-Pr | |
| I-210 | $C_2F_5$ | m = 0 | n-Pr | $CO_2$i-Pr | |
| I-211 | $C_2F_5$ | m = 0 | n-Pr | COMe | |
| I-212 | $C_2F_5$ | m = 0 | n-Pr | COEt | |
| I-213 | $C_2F_5$ | m = 0 | n-Pr | OMe | |
| I-214 | $C_2F_5$ | m = 0 | n-Pr | OEt | |
| I-215 | $C_2F_5$ | m = 0 | n-Pr | O-n-Pr | |
| I-216 | $C_2F_5$ | m = 0 | n-Pr | Et | |
| I-217 | $C_2F_5$ | m = 0 | n-Pr | n-Pr | |
| I-218 | $C_2F_5$ | m = 0 | n-Pr | i-Bu | |
| I-219 | $C_2F_5$ | m = 0 | OMe | $CO_2Me$ | |
| I-220 | $C_2F_5$ | m = 0 | OMe | $CO_2Et$ | |
| I-221 | $C_2F_5$ | m = 0 | OMe | $CO_2$n-Pr | |
| I-222 | $C_2F_5$ | m = 0 | OMe | $CO_2$i-Pr | |
| I-223 | $C_2F_5$ | m = 0 | OMe | COMe | |
| I-224 | $C_2F_5$ | m = 0 | OMe | COEt | |
| I-225 | $C_2F_5$ | m = 0 | OMe | OMe | |
| I-226 | $C_2F_5$ | m = 0 | OMe | OEt | |
| I-227 | $C_2F_5$ | m = 0 | OMe | O-n-Pr | |
| I-228 | $C_2F_5$ | m = 0 | OMe | Et | |
| I-229 | $C_2F_5$ | m = 0 | OMe | n-Pr | |
| I-230 | $C_2F_5$ | m = 0 | OMe | i-Bu | |
| I-231 | n-$C_3F_7$ | m = 0 | H | $CO_2Et$ | |
| I-232 | n-$C_3F_7$ | m = 0 | H | $CO_2$n-Pr | |
| I-233 | n-$C_3F_7$ | m = 0 | H | $CO_2$i-Pr | |
| I-234 | n-$C_3F_7$ | m = 0 | H | COMe | |
| I-235 | n-$C_3F_7$ | m = 0 | H | COEt | |
| I-236 | n-$C_3F_7$ | m = 0 | H | OMe | |
| I-237 | n-$C_3F_7$ | m = 0 | H | O-n-Pr | |
| I-238 | n-$C_3F_7$ | m = 0 | H | Et | |
| I-239 | n-$C_3F_7$ | m = 0 | H | n-Pr | |
| I-240 | n-$C_3F_7$ | m = 0 | H | i-Bu | |
| I-241 | n-$C_3F_7$ | m = 0 | Me | $CO_2Et$ | |
| I-242 | n-$C_3F_7$ | m = 0 | Me | $CO_2$n-Pr | |

TABLE 1 (I)-continued

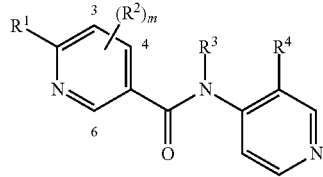

| No. | R¹ | (R²)m | R³ | R⁴ | Physical properties |
|---|---|---|---|---|---|
| I-243 | n-$C_3F_7$ | m = 0 | Me | $CO_2$i-Pr | |
| I-244 | n-$C_3F_7$ | m = 0 | Me | COMe | |
| I-245 | n-$C_3F_7$ | m = 0 | Me | COEt | |
| I-246 | n-$C_3F_7$ | m = 0 | Me | OMe | |
| I-247 | n-$C_3F_7$ | m = 0 | Me | O-n-Pr | |
| I-248 | n-$C_3F_7$ | m = 0 | Me | Et | |
| I-249 | n-$C_3F_7$ | m = 0 | Me | n-Pr | |
| I-250 | n-$C_3F_7$ | m = 0 | Me | i-Bu | |
| I-251 | n-$C_3F_7$ | m = 0 | Et | $CO_2Et$ | |
| I-252 | n-$C_3F_7$ | m = 0 | Et | $CO_2$n-Pr | |
| I-253 | n-$C_3F_7$ | m = 0 | Et | $CO_2$i-Pr | |
| I-254 | n-$C_3F_7$ | m = 0 | Et | COMe | |
| I-255 | n-$C_3F_7$ | m = 0 | Et | COEt | |
| I-256 | n-$C_3F_7$ | m = 0 | Et | OMe | |
| I-257 | n-$C_3F_7$ | m = 0 | Et | O-n-Pr | |
| I-258 | n-$C_3F_7$ | m = 0 | Et | Et | |
| I-259 | n-$C_3F_7$ | m = 0 | Et | n-Pr | |
| I-260 | n-$C_3F_7$ | m = 0 | Et | i-Bu | |
| I-261 | n-$C_3F_7$ | m = 0 | n-Pr | $CO_2Me$ | |
| I-262 | n-$C_3F_7$ | m = 0 | n-Pr | $CO_2Et$ | |
| I-263 | n-$C_3F_7$ | m = 0 | n-Pr | $CO_2$n-Pr | |
| I-264 | n-$C_3F_7$ | m = 0 | n-Pr | $CO_2$i-Pr | |
| I-265 | n-$C_3F_7$ | m = 0 | n-Pr | COMe | |
| I-266 | n-$C_3F_7$ | m = 0 | n-Pr | COEt | |
| I-267 | n-$C_3F_7$ | m = 0 | n-Pr | OMe | |
| I-268 | n-$C_3F_7$ | m = 0 | n-Pr | OEt | |
| I-269 | n-$C_3F_7$ | m = 0 | n-Pr | O-n-Pr | |
| I-270 | n-$C_3F_7$ | m = 0 | n-Pr | Et | |
| I-271 | n-$C_3F_7$ | m = 0 | n-Pr | n-Pr | |
| I-272 | n-$C_3F_7$ | m = 0 | n-Pr | i-Bu | |
| I-273 | n-$C_3F_7$ | m = 0 | OMe | $CO_2Me$ | |
| I-274 | n-$C_3F_7$ | m = 0 | OMe | $CO_2Et$ | |
| I-275 | n-$C_3F_7$ | m = 0 | OMe | $CO_2$n-Pr | |
| I-276 | n-$C_3F_7$ | m = 0 | OMe | $CO_2$i-Pr | |
| I-277 | n-$C_3F_7$ | m = 0 | OMe | COMe | |
| I-278 | n-$C_3F_7$ | m = 0 | OMe | COEt | |
| I-279 | n-$C_3F_7$ | m = 0 | OMe | OMe | |
| I-280 | n-$C_3F_7$ | m = 0 | OMe | OEt | |
| I-281 | n-$C_3F_7$ | m = 0 | OMe | O-n-Pr | |
| I-282 | n-$C_3F_7$ | m = 0 | OMe | Et | |
| I-283 | n-$C_3F_7$ | m = 0 | OMe | n-Pr | |
| I-284 | n-$C_3F_7$ | m = 0 | OMe | i-Bu | |
| I-285 | i-$C_3F_7$ | m = 0 | H | $CO_2Et$ | |
| I-286 | i-$C_3F_7$ | m = 0 | H | $CO_2$n-Pr | |
| I-287 | i-$C_3F_7$ | m = 0 | H | $CO_2$i-Pr | |
| I-288 | i-$C_3F_7$ | m = 0 | H | COMe | |
| I-289 | i-$C_3F_7$ | m = 0 | H | COEt | |
| I-290 | i-$C_3F_7$ | m = 0 | H | OMe | |
| I-291 | i-$C_3F_7$ | m = 0 | H | OEt | |
| I-292 | i-$C_3F_7$ | m = 0 | H | O-n-Pr | |
| I-293 | i-$C_3F_7$ | m = 0 | H | Et | |
| I-294 | i-$C_3F_7$ | m = 0 | H | n-Pr | |
| I-295 | i-$C_3F_7$ | m = 0 | H | i-Bu | |
| I-296 | i-$C_3F_7$ | m = 0 | Me | $CO_2Et$ | |
| I-297 | i-$C_3F_7$ | m = 0 | Me | $CO_2$n-Pr | |
| I-298 | i-$C_3F_7$ | m = 0 | Me | $CO_2$i-Pr | |
| I-299 | i-$C_3F_7$ | m = 0 | Me | COMe | |
| I-300 | i-$C_3F_7$ | m = 0 | Me | COEt | |
| I-301 | i-$C_3F_7$ | m = 0 | Me | OMe | |
| I-302 | i-$C_3F_7$ | m = 0 | Me | OEt | |
| I-303 | i-$C_3F_7$ | m = 0 | Me | O-n-Pr | |
| I-304 | i-$C_3F_7$ | m = 0 | Me | Et | |
| I-305 | i-$C_3F_7$ | m = 0 | Me | n-Pr | |
| I-306 | i-$C_3F_7$ | m = 0 | Me | i-Bu | |
| I-307 | i-$C_3F_7$ | m = 0 | Et | $CO_2Et$ | |
| I-308 | i-$C_3F_7$ | m = 0 | Et | $CO_2$n-Pr | |

TABLE 1 (I)-continued

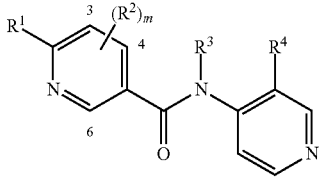

(I)

| No. | R¹ | (R²)m | R³ | R⁴ | Physical properties |
|---|---|---|---|---|---|
| I-309 | i-$C_3F_7$ | m = 0 | Et | $CO_2$i-Pr | |
| I-310 | i-$C_3F_7$ | m = 0 | Et | COMe | |
| I-311 | i-$C_3F_7$ | m = 0 | Et | COEt | |
| I-312 | i-$C_3F_7$ | m = 0 | Et | OMe | |
| I-313 | i-$C_3F_7$ | m = 0 | Et | OEt | |
| I-314 | i-$C_3F_7$ | m = 0 | Et | O-n-Pr | |
| I-315 | i-$C_3F_7$ | m = 0 | Et | Et | |
| I-316 | i-$C_3F_7$ | m = 0 | Et | n-Pr | |
| I-317 | i-$C_3F_7$ | m = 0 | Et | i-Bu | |
| I-318 | i-$C_3F_7$ | m = 0 | OMe | $CO_2$Me | |
| I-319 | i-$C_3F_7$ | m = 0 | OMe | $CO_2$Et | |
| I-320 | i-$C_3F_7$ | m = 0 | OMe | $CO_2$n-Pr | |
| I-321 | i-$C_3F_7$ | m = 0 | OMe | $CO_2$i-Pr | |
| I-322 | i-$C_3F_7$ | m = 0 | OMe | COMe | |
| I-323 | i-$C_3F_7$ | m = 0 | OMe | COEt | |
| I-324 | i-$C_3F_7$ | m = 0 | OMe | OMe | |
| I-325 | i-$C_3F_7$ | m = 0 | OMe | OEt | |

TABLE 1 (I)-continued

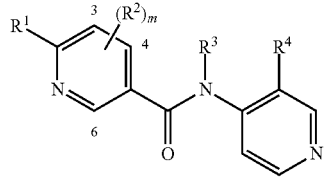

(I)

| No. | R¹ | (R²)m | R³ | R⁴ | Physical properties |
|---|---|---|---|---|---|
| I-326 | i-$C_3F_7$ | m = 0 | OMe | O-n-Pr | |
| I-327 | i-$C_3F_7$ | m = 0 | OMe | Et | |
| I-328 | i-$C_3F_7$ | m = 0 | OMe | n-Pr | |
| I-329 | i-$C_3F_7$ | m = 0 | OMe | i-Bu | |
| I-330 | $CF_3$ | m = 0 | cyc-Pr | $CO_2$Me | 143.6 |
| I-331 | $CF_3$ | m = 0 | cyc-Pr | $CO_2$Et | |
| I-332 | $CF_3$ | m = 0 | cyc-Pr | $CO_2$n-Pr | |
| I-333 | $CF_3$ | m = 0 | cyc-Pr | $CO_2$i-Pr | |
| I-334 | $CF_3$ | m = 0 | cyc-Pr | COMe | |
| I-335 | $CF_3$ | m = 0 | cyc-Pr | COEt | |
| I-336 | $CF_3$ | m = 0 | cyc-Pr | OMe | |
| I-337 | $CF_3$ | m = 0 | cyc-Pr | OEt | |
| I-338 | $CF_3$ | m = 0 | cyc-Pr | O-n-Pr | |
| I-339 | $CF_3$ | m = 0 | cyc-Pr | Et | |
| I-340 | $CF_3$ | m = 0 | cyc-Pr | n-Pr | |
| I-341 | $CF_3$ | m = 0 | cyc-Pr | i-Bu | |

TABLE 2

| No. | ¹H-NMR δ values ppm Measuring device: JEOL-ECX(500 MHz), Solvent: CDCl3 |
|---|---|
| I-3 | 9.25 (1H, s), 8.63 (1H, s), 8.51-8.55 (2H, m), 8.43 (2H, dd), 7.90 (1H, d) |
| I-4 | 9.25 (1H, s), 8.72 (1H, s), 8.49-8.58 (3H, m), 8.43 (1H, d), 7.89 (1H, d) |
| I-8 | 8.57 (1H, brs), 8.35 (1H, d), 8.28 (2H, d), 7.88 (1H, d), 7.05 (1H, d), 6.61 (2H, brs), 4.28 (2H, q), 1.53 (3H, t) |
| I-17 | 12.26 (1H, brs), 9.24 (1H, s), 9.07 (1H, s), 8.75 (1H, d), 8.71 (1H, d), 8.27 (1H, dd), 7.52 (1H, d), 4.05 (3H, s) |
| I-19 | 12.19 (1H, brs), 9.22 (1H, s), 9.19 (1H, d), 8.78 (1H, d), 8.69 (1H, d), 8.20 (1H, dd), 7.34 (1H, d), 4.02 (3H, s), 2.67 (3H, s) |
| I-23 | 9.22 (1H, s), 9.85 (1H, d), 8.66-8.69 (2H, m), 7.46 (1H, d), 4.30 (3H, s), 4.01 (3H, s) |
| I-26 | 8.75 (1H, s), 8.69 (1H, s), 8.478-8.51 (3H, m), 8.20 (1H, d), 7.01 (1H, d), 4.85 (2H, q) |
| I-27 | 12.18 (1H, s), 9.21 (1H, s), 8.86 (1H, s), 8.75 (1H, d), 8.68 (1H, d), 8.28 (1H, d), 7.00 (1H, d), 4.85 (2H, q), 4.02 (3H, s) |
| I-29 | 9.15 (1H, s), 8.87 (1H, s), 8.41-8.52 (3H, m), 8.22 (1H, dd), 7.54 (1H, d), 1.42 (9H, s) |
| I-36 | 9.36 (1H, s), 9.05 (1H, s), 8.90 (1H, d), 8.23 (1H, dd), 7.79 (1H, d), 7.30 (1H, d), 3.92 (3H, s), 3.67 (3H, s) |
| I-50 | 9.05 (1H, brs), 8.69 (1H, brs), 8.64 (1H, brs), 7.84 (1H, brs), 7.55 (1H, brs), 7.25 (1H, m), 4.15 (2H, q), 3.88 (3H, brs), 1.25 (3H, t) |
| I-51 | 9.02 (1H, s), 8.71 (1H, d), 8.07 (1H, br), 7.70 (1H, d), 7.38 (2H, t), 7.19 (2H, m), 7.06 (2H, d), 6.77 (1H, d), 3.93 (2H, br), 3.85 (3H, s), 1.22 (3H, t) |
| I-54 | 9.26 9.13 (1H, s), 9.10 8.58 (1H, s), 8.92 8.87 (1H, d), 8.64 8.56 (1H, d), 7.65 7.30 (1H, d), 7.47 6.92 (1H, d), 4.05 3.98 (3H, s), 3.18-4.62 (2H, m), 1.19 1.06 (3H, t) |
| I-56 | 9.22 (1H, brs), 9.16 (1H, s), 8.61-8.89 (2H, m) 8.24 (d, 1H), 4.06 (3H, s) |
| I-71 | 8.66 (1H, s), 8.22 (1H, d), 8.20 (1H, s), 7.81 (1H, dd), 7.51 (1H, d), 7.07 (1H, d), 4.03 (2H, br), 3.91 (2H, br), 1.41 (3H, t), 1.21 (3H, t) |
| I-76 | 8.65 (1H, s), 8.25 (1H, d), 8.22 (1H, s), 7.81 (1H, d), 7.52 (1H, d), 7.08 (1H, d), 3.92 (2H, br), 3.79 (3H, s), 1.20 (3H, t) |
| I-88 | 9.49 (1H, d), 9.28 (1H, s), 8.79 (1H, d), 8.75 (1H, d), 8.72 (1H, d), 4.06 (3H, s) |
| I-108 | 9.03 (1H, br), 8.74 (1H, br), 8.62 (1H, br), 7.81 (1H, br), 7.52 (1H, br), 7.20 (1H, br), 4.34 (2H, q), 4.12 (2H, q), 1.36 (3H, t), 1.26 (3H, t) |

Test Example 1

Test on Effect Against Brown Planthopper (*Nilaparvata lugens*)

Rice seedling was subjected to a dipping treatment in a test solution prepared so that the concentration of a compound of the present invention be 200 ppm. After the test solution was dried in air, the seedling with its root wrapped with a wet absorbent cotton, was put into a test tube. Then, about 10 second- to third-instar nymphs of brown planthopper (*Nilaparvata lugens*) were released therein, and the tube was covered with a gauze and left in a chamber with lighting at 25° C. On the fifth day after the treatment, life or death of the brown planthopper (*Nilaparvata lugens*) was judged, and the mortality (%) was determined by the following equation. As a result of testing Compound Nos. I-4, I-8, I-9, I-10, I-11, and I-94, the mortality was shown to be 90% or more for all compounds.

Mortality (%)=(Number of dead insects/Number of released insects)×100

Test Example 2

Test on Effect Against Sweetpotato Whitefly (*Bemisia tabaci*)

Adults of sweetpotato whitefly (*Bemisia tabaci*) were released on cucumber seedling planted in a pot. After they were permitted to lay eggs for 1 day, the cucumber seedling was taken out and left in a chamber with lighting at 25° C. After 7 days, the number of first- to second-instar nymphs parasitic on the cucumber seedling was investigated and a test solution prepared so that the concentration of a compound of the present invention be 200 ppm was sprayed using a hand sprayer. After the test solution was dried in air, the cucumber seedling was left in a chamber with lighting at 25° C. On seventh day after the treatment, the number of old nymphs was investigated and the control value was determined by the following equation. As a result of testing Compound Nos. I-7, I-8, I-9, I-10, I-11, I-12, I-13, I-15, I-25, I-27, I-29, I-30, and I-94, the control value was shown to be 90% or more for all compounds.

Control value=(1−(Ta×Cb)/(Tb×Ca))×100

Ta: the number of old nymphs after treatment on treated cucumber seedling
Tb: the number of first- to second-instar nymphs before treatment on treated cucumber seedling
Ca; the number of old nymphs after treatment on non-treated cucumber seedling
Cb: the number of first- to second-instar nymphs before treatment on non-treated cucumber seedling Test Example 3

Test on Effect Against Green Peach Aphid (*Myzus persicae*)

5 adults of green peach aphid (*Myzus persicae*) were released on a radish leaf which was inserted into water in a test tube. The adults were removed after 1 day, the number of nymphs parasitic on the radish leaf was counted, which was subjected to a dipping treatment in a test solution prepared so that the concentration of a compound of the present invention be 200 ppm. After the test solution was dried in air, the leaf was left in a chamber with lighting at 25° C. On the fifth day after the treatment, life or death of the green peach aphid (*Myzus persicae*) was judged, and the mortality was determined by the following equation. Incidentally, removed insects and abnormal insects were regarded as dead insects. As a result of testing Compound Nos. I-3, I-7, I-8, I-9, I-10, I-11, I-15, I-25, I-30, and I-94, the mortality was shown to be 90% or more for all compounds.

Mortality (%)=(Number of dead insects/Number of released insects)×100

The following will describe Formulation Examples.

Formulation Example 1

| | |
|---|---|
| (1) Compound of the present invention | 20 parts by weight |
| (2) Clay | 70 parts by weight |
| (3) White carbon | 5 parts by weight |
| (4) Sodium polycarboxylate | 3 parts by weight |
| (5) Sodium alkylnaphthalenesulfonate | 2 parts by weight |

The above ones are uniformly mixed to form a wettable powder.

Formulation Example 2

| | |
|---|---|
| (1) Compound of the present invention | 5 parts by weight |
| (2) Talc | 60 parts by weight |
| (3) Calcium carbonate | 34.5 parts by weight |
| (4) Liquid paraffin | 0.5 parts by weight |

The above ones are uniformly mixed to form a dust.

Formulation Example 3

| | |
|---|---|
| (1) Compound of the present invention | 20 parts by weight |
| (2) N,N-Dimethylacetamide | 20 parts by weight |
| (3) Polyoxyethylene tristyryl phenyl ether | 10 parts by weight |
| (4) Calcium dodecylbenzenesulfonate | 2 parts by weight |
| (5) Xylene | 48 parts by weight |

The above ones are uniformly mixed and dissolved to form an emulsifiable concentrate.

Formulation Example 4

| | |
|---|---|
| (1) Clay | 68 parts by weight |
| (2) Sodium ligninsulfonate | 2 parts by weight |
| (3) Polyoxyethylene alkylaryl sulfate | 5 parts by weight |
| (4) White carbon | 25 parts by weight |

A mixture of the above ingredients and a compound of the present invention were mixed in a weight ratio of 4:1 to form a wettable powder.

Formulation Example 5

| | |
|---|---|
| (1) Compound of the present invention | 50 parts by weight |
| (2) Condensate of sodium alkylnaphthalenesulfonate with formaldehyde | 2 parts by weight |
| (3) Silicone oil | 0.2 part by weight |
| (4) Water | 47.8 parts by weight |

The above ones are uniformly mixed and pulverized to form a raw liquid. To the raw liquid are further added

| (5) Sodium polycarboxylate | 5 parts by weight |
| (6) Anhydrous sodium sulfate | 42.8 parts by weight, | and the whole is uniformly mixed, granulated, and dried to obtain water dispersible granules.

Formulation Example 6

| (1) Compound of the present invention | 5 parts by weight |
| (2) Polyoxyethylene octylphenyl ether | 1 part by weight |
| (3) Polyoxyethylene alkyl ether phosphate ester | 0.1 part by weight |
| (4) Particulate calcium carbonate | 93.9 parts by weight |

The above (1) to (3) are uniformly mixed previously and, after diluted with an appropriate amount of acetone, the diluted mixture was sprayed to the above (4) and acetone is removed to form granules.

Formulation Example 7

| (1) Compound of the present invention | 2.5 parts by weight |
| (2) N,N-Dimethylacetamide | 2.5 parts by weight |
| (3) Soybean oil | 95.0 parts by weight |

The above ones are uniformly mixed and dissolved to form a ultra low volume formulation.

Formulation Example 8

| (1) Compound of the present invention | 10 parts by weight |
| (2) Diethylene glycol monoethyl ether | 80 parts by weight |
| (3) Polyoxyethylene alkyl ether | 10 parts by weight |

The above ones are uniformly mixed to form a soluble concentrate.

While the present invention has been described in detail or with reference to specific embodiments thereof, it will be apparent to one ordinary in the art that various changes and modifications can be made therein without departing from the spirit and scope of the present invention. The present application is based on Japanese Patent Application No. 2017-088847 filed on Apr. 27, 2017, and the contents are incorporated herein by reference.

The invention claimed is:

1. An N-(4-pyridyl)nicotinamide compound represented by formula (I):

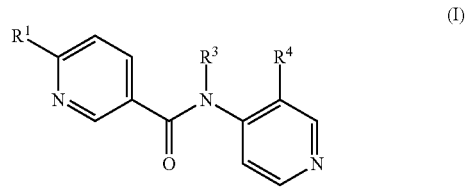

wherein $R^1$ is a trifluoromethyl group;
$R^3$ is a hydrogen atom, a $(C_1\text{-}C_6)$-alkyl, or a $(C_3\text{-}C_6)$-cycloalkyl; and
$R^4$ is a $(C_1\text{-}C_6)$-alkyl, a $(C_1\text{-}C_6)$-alkoxy, a $(C_1\text{-}C_6)$-alkylcarbonyl, or a $(C_1\text{-}C_6)$-alkoxycarbonyl;
or a salt thereof.

2. An agricultural and horticultural insecticide, miticide, or nematicide comprising the compound or a salt thereof of according to claim 1 as an active ingredient and an additive.

3. An agricultural and horticultural insecticide, miticide, or nematicide comprising the compound or a salt thereof of according to claim 1 as an active ingredient.

4. A method for controlling a horticultural pest or an agricultural pest, comprising applying an effective amount of the compound or a salt thereof according to claim 1 to a plant, soil, the horticultural pest, or the agricultural pest,
wherein the horticultural pest or the agricultural pest is selected from the group consisting of aphids, diamondback moth, cabbage armyworm, common cutworm, codling moth, corn earworm moth, tobacco budworm, gypsy moth, rice leafroller, smaller tea tortrix, colorado potato beetle, cucurbit leaf beetle, boll weevil, planthoppers, leafhoppers, scales, stinkbugs, whiteflies, thrips, grasshoppers, anthomyiid flies, scarabaeidae scarabs, black cutworm, turnip moth cutworm, ants, gastropods, sanitary hygienic insect pests, cockroaches, housefly, house mosquito, household insect pests, mites, house dust mites, and nematodes.

* * * * *